(12) United States Patent
Connor

(10) Patent No.: US 11,478,158 B2
(45) Date of Patent: Oct. 25, 2022

(54) WEARABLE RING OF OPTICAL BIOMETRIC SENSORS

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 349 days.

(21) Appl. No.: 16/568,580

(22) Filed: Sep. 12, 2019

(65) Prior Publication Data
US 2020/0000345 A1    Jan. 2, 2020

Related U.S. Application Data

(63) Continuation-in-part of application No. 15/963,061, filed on Apr. 25, 2018, now Pat. No. 10,772,559, and a continuation-in-part of application No. 15/725,330, filed on Oct. 5, 2017, now Pat. No. 10,607,507, which is a continuation-in-part of application No. 15/431,769, filed on Feb. 14, 2017, now abandoned, application No. 16/568,580, which is a continuation-in-part of application No. 15/431,769, filed on Feb. 14, 2017, now abandoned, and a continuation-in-part of application No. 15/418,620,
(Continued)

(51) Int. Cl.
| A61B 5/1455 | (2006.01) |
| A61B 5/0205 | (2006.01) |
| A61B 5/145 | (2006.01) |
| A61B 5/00 | (2006.01) |
| A61B 5/021 | (2006.01) |
| A61B 5/024 | (2006.01) |

(52) U.S. Cl.
CPC ........ *A61B 5/0205* (2013.01); *A61B 5/14532* (2013.01); *A61B 5/14551* (2013.01); *A61B 5/4875* (2013.01); *A61B 5/681* (2013.01); *A61B 5/021* (2013.01); *A61B 5/02405* (2013.01); *A61B 5/02416* (2013.01); *A61B 5/02438* (2013.01); *A61B 5/6824* (2013.01); *A61B 5/6826* (2013.01); *A61B 2562/0233* (2013.01); *A61B 2562/043* (2013.01)

(58) Field of Classification Search
CPC .............. A61B 5/1455; A61B 5/14551; A61B 5/14552; A61B 5/14532; A61B 5/02438; A61B 5/6826; A61B 5/6838; A61B 5/6814; A61B 5/021; A61B 5/6816; A61B 5/002; A61B 5/0205
See application file for complete search history.

(56) References Cited

U.S. PATENT DOCUMENTS

| 5,524,617 A | * | 6/1996 | Mannheimer | ...... | A61B 5/14551 600/323 |
| 6,285,894 B1 | * | 9/2001 | Oppelt | ................ | A61B 5/1455 600/335 |

(Continued)

*Primary Examiner* — Chu Chuan Liu

(57) ABSTRACT

This invention is a wearable ring of optical biometric sensors comprising an arcuate array of light emitters and light receivers which is configured to collectively span at least half of the circumference of a person's wrist, finger, or arm. Light energy from the light emitters which has passed through the person's body tissue and/or has been reflected from the person's body tissue is analyzed in order to measure biometric parameters such as the person's oxygenation level, hydration level, glucose level, pulse rate, heart rate variability, and/or blood pressure.

2 Claims, 5 Drawing Sheets

Related U.S. Application Data filed on Jan. 27, 2017, now abandoned, said application No. 15/431,769 is a continuation-in-part of application No. 15/294,746, filed on Oct. 16, 2016, now Pat. No. 10,627,861, application No. 16/568,580, which is a continuation-in-part of application No. 15/294,746, filed on Oct. 16, 2016, now Pat. No. 10,627,861, said application No. 15/431,769 is a continuation-in-part of application No. 15/206,215, filed on Jul. 8, 2016, now abandoned, which is a continuation-in-part of application No. 14/951,475, filed on Nov. 24, 2015, now Pat. No. 10,314,492, said application No. 15/418,620 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/725,330 is a continuation-in-part of application No. 14/951,475, filed on Nov. 24, 2015, now Pat. No. 10,314,492, said application No. 15/963,061 is a continuation-in-part of application No. 14/550,953, filed on Nov. 22, 2014, now abandoned, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449.

(60) Provisional application No. 62/857,942, filed on Jun. 6, 2019, provisional application No. 62/814,713, filed on Mar. 6, 2019, provisional application No. 62/814,692, filed on Mar. 6, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/297,827, filed on Feb. 20, 2016, provisional application No. 62/245,311, filed on Oct. 23, 2015.

(56) References Cited

U.S. PATENT DOCUMENTS

| | | |
|---|---|---|
| 7,371,217 B2 | 5/2008 | Kim et al. |
| 8,725,226 B2 | 5/2014 | Isaacson |
| 8,868,149 B2 | 10/2014 | Eisen et al. |
| 9,149,216 B2 | 10/2015 | Eisen et al. |
| 9,314,197 B2 | 4/2016 | Eisen et al. |
| 9,498,158 B2 | 11/2016 | Isaacson |
| 9,642,578 B2 | 5/2017 | Newberry |
| 9,730,622 B2 | 8/2017 | Eisen et al. |
| 9,980,676 B2 | 5/2018 | Newberry |
| 10,317,200 B1 | 6/2019 | Han et al. |
| 10,321,860 B2 | 6/2019 | Newberry |
| 10,349,847 B2 | 7/2019 | Kwon et al. |
| 10,357,165 B2 | 7/2019 | Yoon |
| 10,401,800 B2 | 9/2019 | Cardinal et al. |
| 2002/0169381 A1* | 11/2002 | Asada ............... A61B 5/14552 600/485 |
| 2002/0173709 A1* | 11/2002 | Fine ................. A61B 5/14552 600/335 |
| 2006/0122520 A1* | 6/2006 | Banet ............... A61B 5/14552 600/503 |
| 2011/0046464 A1* | 2/2011 | Debreczeny ......... A61B 5/6826 600/335 |
| 2011/0082355 A1 | 4/2011 | Eisen et al. |
| 2012/0296178 A1* | 11/2012 | Lamego ............. A61B 5/1455 600/310 |
| 2013/0131475 A1 | 5/2013 | Eisen et al. |
| 2014/0058226 A1 | 2/2014 | Chernobro et al. |
| 2014/0200423 A1 | 7/2014 | Eisen et al. |
| 2015/0105638 A1 | 4/2015 | Eisen et al. |
| 2016/0146726 A1 | 5/2016 | Aggarwal |
| 2016/0206251 A1 | 7/2016 | Kwon et al. |
| 2016/0262673 A1 | 9/2016 | Skorich et al. |
| 2016/0278676 A1 | 9/2016 | Eisen et al. |
| 2016/0338601 A1 | 11/2016 | Yang |
| 2017/0071518 A1 | 3/2017 | Xavier Da Silveira et al. |
| 2017/0196493 A1 | 7/2017 | Isaacson |
| 2017/0209095 A1 | 7/2017 | Wagner et al. |
| 2017/0224263 A1 | 8/2017 | Lobbestael et al. |
| 2017/0231566 A1 | 8/2017 | Klimek et al. |
| 2017/0303788 A1 | 10/2017 | Xavier Da Silveira et al. |
| 2017/0311823 A1 | 11/2017 | Rausch et al. |
| 2017/0319131 A1 | 11/2017 | Xavier Da Silveira et al. |
| 2017/0325742 A1 | 11/2017 | Prior et al. |
| 2018/0020979 A1 | 1/2018 | Wagner et al. |
| 2018/0042554 A1 | 2/2018 | Wagner et al. |
| 2018/0055449 A1 | 3/2018 | Ko et al. |
| 2018/0070850 A1 | 3/2018 | Stafford et al. |
| 2018/0074010 A1 | 3/2018 | Wang et al. |
| 2018/0074011 A1 | 3/2018 | Wang et al. |
| 2018/0074012 A1 | 3/2018 | Wang et al. |
| 2018/0078209 A1 | 3/2018 | Wagner et al. |
| 2018/0103883 A1 | 4/2018 | Darty et al. |
| 2018/0140237 A1 | 5/2018 | Rajan et al. |
| 2018/0140238 A1 | 5/2018 | Johnson et al. |
| 2018/0143150 A1 | 5/2018 | Bezemer et al. |
| 2018/0220906 A1 | 8/2018 | LeBoeuf et al. |
| 2018/0271448 A1 | 9/2018 | Bynam et al. |
| 2018/0317786 A1 | 11/2018 | Kulach et al. |
| 2018/0325431 A1 | 11/2018 | Guarin et al. |
| 2018/0333107 A1 | 11/2018 | Garcia Sada et al. |
| 2019/0013368 A1 | 1/2019 | Chung et al. |
| 2019/0025120 A1 | 1/2019 | Lee et al. |
| 2019/0049296 A1 | 2/2019 | Cho et al. |
| 2019/0067257 A1 | 2/2019 | Yeon et al. |
| 2019/0069843 A1 | 3/2019 | Chatterjee et al. |
| 2019/0104942 A1 | 4/2019 | Peru et al. |
| 2019/0113387 A1 | 4/2019 | Lee et al. |
| 2019/0117140 A1 | 4/2019 | Al-Ali et al. |
| 2019/0120689 A1 | 4/2019 | Leem et al. |
| 2019/0133469 A1 | 5/2019 | Just et al. |
| 2019/0142313 A1 | 5/2019 | Abou Ismail et al. |
| 2019/0150746 A1 | 5/2019 | Kim |
| 2019/0154584 A1 | 5/2019 | Ahn et al. |
| 2019/0159703 A1 | 5/2019 | Aggarwal et al. |
| 2019/0167170 A1 | 6/2019 | Varsavsky et al. |
| 2019/0167190 A1 | 6/2019 | Choi et al. |
| 2019/0167201 A1 | 6/2019 | Xavier Da Silveira et al. |
| 2019/0200883 A1 | 7/2019 | Moon et al. |
| 2019/0216322 A1 | 7/2019 | Anikanov et al. |
| 2019/0216340 A1 | 7/2019 | Holz et al. |
| 2019/0246977 A1 | 8/2019 | Miller et al. |
| 2019/0252569 A1 | 8/2019 | Jo et al. |

\* cited by examiner

WEARABLE RING OF OPTICAL BIOMETRIC SENSORS

CROSS-REFERENCE TO RELATED APPLICATIONS

This application claims the priority benefit of U.S. provisional patent application 62/857,942 filed on Jun. 6, 2019. This application claims the priority benefit of U.S. provisional patent application 62/814,713 filed on Mar. 6, 2019. This application claims the priority benefit of U.S. provisional patent application 62/814,692 filed on Mar. 6, 2019. This application is a continuation in part of U.S. patent application Ser. No. 15/963,061 filed on Mar. 25, 2018. This application is a continuation in part of U.S. patent application Ser. No. 15/725,330 filed on Oct. 5, 2017. This application is a continuation in part of U.S. patent application Ser. No. 15/431,769 filed on Feb. 14, 2017. This application is a continuation in part of U.S. patent application Ser. No. 15/418,620 filed on Jan. 27, 2017. This application is a continuation in part of U.S. patent application Ser. No. 15/294,746 filed on Oct. 16, 2016. U.S. patent application Ser. No. 15/963,061 was a continuation in part of U.S. patent application Ser. No. 14/550,953 filed on Nov. 22, 2014. U.S. patent application Ser. No. 15/725,330 claimed the priority benefit of U.S. provisional patent application 62/549,587 filed on Aug. 24, 2017. U.S. patent application Ser. No. 15/725,330 was a continuation in part of U.S. patent application Ser. No. 15/431,769 filed on Feb. 14, 2017. U.S. patent application Ser. No. 15/725,330 claimed the priority benefit of U.S. provisional patent application 62/439,147 filed on Dec. 26, 2016. U.S. patent application Ser. No. 15/725,330 was a continuation in part of U.S. patent application Ser. No. 14/951,475 filed on Nov. 24, 2015 which issued as U.S. Pat. No. 10,314,492 on Jun. 11, 2019. U.S. patent application Ser. No. 15/431,769 claimed the priority benefit of U.S. provisional patent application 62/439,147 filed on Dec. 26, 2016. U.S. patent application Ser. No. 15/431,769 was a continuation in part of U.S. patent application Ser. No. 15/294,746 filed on Oct. 16, 2016. U.S. patent application Ser. No. 15/431,769 was a continuation in part of U.S. patent application Ser. No. 15/206,215 filed on Jul. 8, 2016. U.S. patent application Ser. No. 15/431,769 claimed the priority benefit of U.S. provisional patent application 62/349,277 filed on Jun. 13, 2016. U.S. patent application Ser. No. 15/431,769 claimed the priority benefit of U.S. provisional patent application 62/311,462 filed on Mar. 22, 2016. U.S. patent application Ser. No. 15/418,620 claimed the priority benefit of U.S. provisional patent application 62/439,147 filed on Dec. 26, 2016. U.S. patent application Ser. No. 15/418,620 claimed the priority benefit of U.S. provisional patent application 62/297,827 filed on Feb. 20, 2016. U.S. patent application Ser. No. 15/418,620 was a continuation in part of U.S. patent application Ser. No. 14/951,475 filed on Nov. 24, 2015 which issued as U.S. Pat. No. 10,314,492 on Jun. 11, 2019. U.S. patent application Ser. No. 15/294,746 claimed the priority benefit of U.S. provisional patent application 62/349,277 filed on Jun. 13, 2016. U.S. patent application Ser. No. 15/294,746 was a continuation in part of U.S. patent application Ser. No. 14/951,475 filed on Nov. 24, 2015 which issued as U.S. Pat. No. 10,314,492 on Jun. 11, 2019. U.S. patent application Ser. No. 15/294,746 claimed the priority benefit of U.S. provisional patent application 62/245,311 filed on Oct. 23, 2015. U.S. patent application Ser. No. 15/206,215 claimed the priority benefit of U.S. provisional patent application 62/349,277 filed on Jun. 13, 2016. U.S. patent application Ser. No. 15/206,215 was a continuation in part of U.S. patent application Ser. No. 14/951,475 filed on Nov. 24, 2015 which issued as U.S. Pat. No. 10,314,492 on Jun. 11, 2019. U.S. patent application Ser. No. 14/951,475 claimed the priority benefit of U.S. provisional patent application 62/245,311 filed on Oct. 23, 2015. U.S. patent application Ser. No. 14/951,475 was a continuation in part of U.S. patent application Ser. No. 14/071,112 filed on Nov. 4, 2013. U.S. patent application Ser. No. 14/951,475 was a continuation in part of U.S. patent application Ser. No. 13/901,131 filed on May 23, 2013 which issued as U.S. Pat. No. 9,536,449 on Jan. 3, 2017. The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable optical devices for measuring biometric parameters.

INTRODUCTION

There are many potential health-related benefits from continuous noninvasive measurement of biometric parameters such as oxygenation level, hydration level, glucose level, pulse rate, heart rate variability, and blood pressure. Considerable progress has been made in recent years toward measuring several of these parameters by incorporating noninvasive spectroscopic sensors into wearable devices such as smart watches and fitness bands.

However, technological challenges remain. For example, spectroscopic measurement of biometric parameters via wearable devices can be confounded by movement of the device relative to a person's body. For example, a smart watch can shift and/or rotate on a person's wrist as a person moves, changing the distance and angle between a smart watch housing and body tissue. Such shifting and/or rotation can also change the region of a person's wrist under the housing. Also, some biometric parameters (such as blood glucose level) are notoriously challenging to measure non-invasively using spectroscopy. The invention disclosed herein addresses these challenges.

REVIEW OF THE RELEVANT ART

U.S. patent application publication 20180020979 (Wagner et al., Jan. 25, 2018, "Optical Adapters for Wearable Monitoring Devices") discloses a wearable optical biometric sensor with stabilizing members. U.S. patent application publication 20180042554 (Wagner et al., Feb. 15, 2018, "Optical Monitoring Apparatus and Methods") discloses a biometric device with a digital camera and a photoplethysmography (PPG) sensor. U.S. patent application publication 20170209095 (Wagner et al., Jul. 27, 2017, "Optical Physiological Sensor Modules with Reduced Signal Noise") discloses a wearable optical biometric sensor with multiple diverging-angle light guides. U.S. patent application publication 20180220906 (LeBoeuf et al., Aug. 9, 2018, "Physiological Monitoring Apparatus and Networks") discloses ear-worn devices for biometric and environmental monitoring. U.S. patent application publication 20190133469 (Just et al., May 9, 2019, "Physiological Monitoring Devices Having Sensing Elements Decoupled from Body Motion") discloses a biometric measuring device with multiple bands to reduce motion artifacts. U.S. patent application publication 20180078209 (Wagner et al., Mar. 22, 2018, "Stabilized Sensor Modules and Monitoring Devices Incorporating Same") discloses a wearable optical biometric sensor with stabilizing protrusions.

U.S. patent application publication 20170196493 (Isaacson, Jul. 13, 2017, "Optical Sensor Path Selection") discloses a device with multiple optical elements and detectors to measure a biometric parameter. U.S. Pat. No. 8,725,226 (Isaacson, May 13, 2014, "Optical Sensor Path Selection") discloses a device with multiple possible pairings of light emitters and detectors to scan different tissue depths for biometric measurement. U.S. Pat. No. 9,498,158 (Isaacson, Nov. 22, 2016, "Optical Sensor Path Selection") discloses a device with multiple light emitters to scan different tissue depths for biometric measurement. U.S. patent application publication 20170311823 (Rausch et al., Nov. 2, 2017, "Optical Trigger for Measurement") discloses detecting and using feature in a photoplethysmogram signal for biometric measurement. U.S. patent application publication 20180140238 (Johnson et al., May 24, 2018, "Regional Oximetry Sleeve for Mobile Device") discloses a mobile computing device with a sleeve. U.S. patent application publication 20160262673 (Skorich et al., Sep. 15, 2016, "Segmented Sensor") discloses an optical biometric sensor with a planar substrate. U.S. patent application publication 20170231566 (Klimek et al., Aug. 17, 2017, "Tissue Interface") discloses a garment with a sensor module for biometric measurement. U.S. patent application publication 20170224263 (Lobbestael et al., Aug. 10, 2017, "Tissue Site Detection") discloses an optical biometric sensor which identifies a particular tissue site. U.S. patent application publication 20170325742 (Prior et al., Nov. 16, 2017, "Universal Fingertip Sensor") discloses a finger-tip-worn optical biometric sensor device.

U.S. Pat. No. 7,371,217 (Kim et al., May 13, 2008 Device for the Non-Invasive Measurement of Blood Glucose Concentration by Millimeter Waves and Method Thereof") discloses using millimeter waves to measure glucose level. U.S. Pat. No. 10,349,847 (Kwon et al., Jul. 6, 2019, "Apparatus for Detecting Bio-Information") and U.S. patent application publication 20160206251 (Kwon et al., Jul. 21, 2016, "Apparatus for Detecting Bio-Information") disclose using a two-dimensional optical array to measure biometric parameters. U.S. patent application publication 20190150746 (Kim, May 23, 2019, "Bio-Information Measuring Apparatus and Bio-Information Measuring Method") discloses a biometric spectroscopy device with a pressure sensor. U.S. patent application publication 20190200883 (Moon et al., Jul. 4, 2019, "Bio-Signal Measuring Apparatus and Operating Method Thereof") discloses a biometric device with optical sensors and impedance sensors. U.S. patent application publication 20190120689 (Leem et al., Apr. 25, 2019, "Combination Sensors and Electronic Devices") discloses a biometric device with stacked infrared sensors. U.S. patent application publication 20190216322 (Anikanov et al., Jul. 18, 2019, "Compact Spectrometer System for Non-Invasive Measurement of Absorption and Transmission Spectra in Biological Tissue Samples") discloses a spectrometer for analyzing an inhomogeneous scattering medium.

U.S. patent application publication 20190167190 (Choi et al., Jun. 6, 2019, "Healthcare Apparatus and Operating Method Thereof") discloses using light emitters with different wavelengths to measure blood glucose. U.S. patent application publication 20190049296 (Cho et al., Feb. 14, 2019, "Light Filter and Spectrometer Including the Light Filter") discloses a spectrometer with different spectrum modulation portions. U.S. patent application publication 20190067257 (Yoon et al., Feb. 28, 2019, "Light-Emitting Diode (LED) Device") discloses a multi-color display includes a plurality of light-emitting cells at least partially defined by a partition layer. U.S. Pat. No. 10,357,165 (Yoon, Jul. 23, 2019, "Method and Apparatus for Acquiring Bioinformation and Apparatus for Testing Bioinformation") discloses a biometric sensor analyzing laser speckle patterns. U.S. patent application publication 20180271448 (Bynam et al., Sep. 27, 2018, "Method of Enabling Feature Extraction for Glucose Monitoring Using Near-Infrared (NIR) Spectroscopy") discloses using near-infrared (NIR) spectroscopy to measure blood glucose. U.S. patent application publication 20190013368 (Chung et al., Jan. 10, 2019, "Near-Infrared Light Organic Sensors, Embedded Organic Light Emitting Diode Panels, and Display Devices Including the Same") discloses using an OLED stack for biometric measurement.

U.S. patent application publication 20190252569 (Jo et al., Aug. 15, 2019, "Near-Infrared Light Sensors Including 2-Dimensional Insulator") discloses a near infrared light sensor with a 2D material semiconductor layer on a substrate. U.S. patent application publication 20190025120 (Lee et al., Jan. 24, 2019, "Spectrometer and Spectrum Measurement Method Utilizing Same") discloses a spectrometer with light emitters in different wavelengths or spectra. U.S. patent application publication 20190113387 (Lee et al., Apr. 18, 2019, "Spectrometric Sensor Control Method and Electronic Device for Supporting Same") discloses spectroscopic sensor with multiple wavelength bands. U.S. patent application publication 20190154584 (Ahn et al., May 23, 2019, "Spectroscopy Apparatus, Spectroscopy Method, and Bio-Signal Measuring Apparatus") discloses a spectroscopic apparatus which disperses light at different angles. U.S. patent application publication 20190159703 (Aggarwal et al., May 30, 2019, "System and Method for Obtaining Blood Glucose Concentration Using Temporal Independent Component Analysis (ICA)") discloses using near infrared spectroscopy (NIR) to measure blood glucose. U.S. patent application publication 20180055449 (Ko et al., Mar. 1, 2018, "Wearable Measurement Apparatus") discloses a wearable biometric device with elastic portions.

U.S. Pat. No. 10,401,800 (Cardinali et al., Sep. 3, 2019, "Indicators for Wearable Electronic Devices") discloses a wearable device with a biometric sensor and illuminated biometric status indicator. U.S. Pat. No. 10,317,200 (Han et al., Jun. 11, 2019, "Multi-Mode Sensor for Surface Orientation") discloses a wearable device with an orientation sensor and multiple pairings between light emitters and light detectors. U.S. patent application publication 20180317786 (Kulach et al., Nov. 8, 2018, "Pulse Spectroscopy") discloses a wearable photoplethysmogram (PPG) sensor. U.S. patent application publication 20190216340 (Holz et al., Jul. 18, 2019, "Sensor Device") discloses a multi-dimensional optical sensor for biometric measurements. U.S. patent application publication 20190069843 (Chatterjee et al., Mar. 7, 2019, "Wearable Personal Information System") discloses a wearable optical device with a shield to block ambient light.

U.S. patent application publication 20170071518 (Xavier Da Silveira et al., Mar. 16, 2017, "Apparatus and Method for Optical Tissue Detection") discloses optical discrimination between body tissue and non-tissue materials. U.S. patent application publication 20180140237 (Rajan et al., May 24, 2018, "Device and Method for Determining Biological Indicator Levels in Tissue") discloses using at least two light emitters to measure a biological parameter. U.S. patent application publication 20170319131 (Xavier Da Silveira et al., Nov. 9, 2017, "Method and Device for Hydration Monitoring") discloses using three different wavelengths to measure hydration. U.S. patent application publication 20170303788 (Xavier Da Silveira et al., Oct. 26, 2017, "Wearable Device for Tissue Monitoring With Effective Ambient Light Blocking") discloses an optical biometric device with a shield to block ambient light.

U.S. Pat. No. 8,868,149 (Eisen et al., Oct. 21, 2014, "Photoplethysmography Device and Method") and U.S. Pat. No. 9,149,216 (Eisen et al., Oct. 6, 2015, "Photoplethysmography Device and Method") and U.S. patent application publications 20110082355 (Eisen et al., Apr. 7, 2011, "Photoplethysmography Device and Method"), 20130131475 (Eisen et al., May 23, 2013, "Photoplethysmography Device and Method"), and 20150105638 (Eisen et al., Apr. 16, 2015, "Photoplethysmography Device and Method") disclose using photoplethysmography and dynamic light scattering for biometric measurement. U.S. Pat. No. 9,314,197 (Eisen et al., Apr. 19, 2016, "Wearable Pulse Oximetry Device") and U.S. patent application publication 20140200423 (Eisen et al., Jul. 17, 2014, "Wearable Pulse Oximetry Device") disclose a wrist-worn pulse oximetry device which is worn over the ulna. U.S. Pat. No. 9,730,622 (Eisen et al., Aug. 15, 2017, "Wearable Pulse Oximetry Device") and U.S. patent application publication 20160278676 (Eisen et al., Sep. 29, 2016, "Wearable Pulse Oximetry Device") disclose a wearable pulse oximetry device with two light emitters with two different wavelengths. U.S. patent application publication 20190117140 (Al-Ali et al., Apr. 25, 2019, "Advanced Pulse Oximetry Sensor") discloses a pulse oximetry sensor with a light diffuser and light concentrator. U.S. patent application publication 20160338601 (Yang; Shuchen, Nov. 24, 2016, "Optical Fiber Continuous Detecting Blood Sensor and Wearing Apparatus Thereof") discloses using optical fibers and spectroscopic sensors to measure blood pressure.

U.S. patent application publications 20180074010 (Wang et al., Mar. 15, 2018, "Application of Electrochemical Impedance Spectroscopy in Sensor Systems, Devices, and Related Methods" and 20180074011 (Wang et al., Mar. 15, 2018, "Application of Electrochemical Impedance Spectroscopy in Sensor Systems, Devices, and Related Methods"), and 20180074012 (Wang et al., Mar. 15, 2018, "Application of Electrochemical Impedance Spectroscopy in Sensor Systems, Devices, and Related Methods") disclose using electrochemical impedance spectroscopy to measure glucose level. U.S. patent application publication 20190167170 (Varsaysky et al., Jun. 6, 2019, "Methods and Systems for Improving the Reliability of Orthogonally Redundant Sensors") discloses using orthogonally redundant sensors to measure glucose level.

U.S. Pat. No. 10,321,860 (Newberry, Jun. 18, 2019, "System and Method for Glucose Monitoring") discloses a glucose biosensor with optical fibers. U.S. Pat. No. 9,642,578 (Newberry, May 9, 2017, "System and Method for Health Monitoring Using a Non-Invasive, Multi-Band Biosensor") and U.S. Pat. No. 9,980,676 (Newberry, May 29, 2018, "System and Method for Health Monitoring Using a Non-Invasive, Multi-Band Biosensor") disclose a PPG sensor which uses multiple wavelengths. U.S. patent application publication 20190246977 (Miller et al., Aug. 15, 2019, "Optical Sensor for Wearable Devices") discloses wearables with spectroscopic sensors using two different light frequencies for biometric measurement.

U.S. patent application publication 20160146726 (Aggarwal, May 26, 2016, "Wearable Device for Detection of Contaminants and Method Thereof") discloses a wearable spectrometer for analyzing the chemical composition of substances. U.S. patent application publication 20140058226 (Chernobro et al., Feb. 27, 2014, "Method and Apparatus for In Vivo Optical Measurement of Blood Glucose Concentration") discloses using differential scattering spectroscopy and Doppler microscopy to measure blood glucose. U.S. patent application publication 20190104942 (Peru et al., Apr. 11, 2019, "Spectroscopic System and Method Therefor") discloses probe which analyzes saliva for biometric measurement. U.S. patent application publication 20180070850 (Stafford et al., Mar. 15, 2018, "Apparatus and Method for Detecting Body Composition and Correlating It With Cognitive Efficiency") discloses a biometric device to measure body hydration and correlate it with cognitive efficiency. U.S. patent application publication 20180103883 (Darty et al., Apr. 19, 2018, "Systems and Methods for Measuring Tissue Oxygenation") discloses using images with different spectral bands to measure tissue oxygenation.

U.S. patent application publication 20180325431 (Guarin et al., Nov. 15, 2018, "Electromagnetic Wave Sensor for Determining a Hydration Status of a Body Tissue In Vivo") discloses using an electromagnetic wave sensor to measure body tissue hydration. U.S. patent application publication 20180143150 (Bezemer et al., May 24, 2018, "Apparatus and Methods That Use Magnetic Induction Spectroscopy to Monitor Tissue Fluid Content") discloses using magnetic induction spectroscopy to measure tissue fluid. U.S. patent application publication 20190142313 (Abou Ismail et al., May 16, 2019, "System and Method for Non-Invasive Continuous Real-Time Blood Glucose Monitoring") discloses using an impedance sensor and permittivity to measure blood glucose. U.S. patent application publication 20190167201 (Xavier Da Silveira et al., Jun. 6, 2019, "Wearable Athletic Monitoring Using Digital Modulation") discloses a wearable spectroscopic sensor with digital modulation. U.S. patent application publication 20180333107 (Garcia Sada et al., Nov. 22, 2018, "Non-Invasive Wearable Device, Process and Systems with Adjustable Operation") discloses a wearable device with a flexible housing and an array of sensors.

As evidenced by the above review of relevant art, there has been considerable innovation in measuring biometric parameters by incorporating noninvasive spectroscopic sensors into wearable devices such as smart watches and fitness bands. However, some technological challenges remain. For example, spectroscopic measurement of biometric parameters via wearable devices can be confounded by movement of the device relative to a person's body. For example, a smart watch can shift and/or rotate on a person's wrist as a person moves, changing the distance and angle between a smart watch housing and body tissue. Such shifting and/or rotation can also change the region of a person's wrist under the housing. Also, some biometric parameters (such as blood glucose level) are notoriously challenging to measure non-invasively using spectroscopy. The invention disclosed herein addresses these challenges.

SUMMARY OF THE INVENTION

This invention is a wearable ring of optical biometric sensors comprising an arcuate array of light emitters and light receivers which is configured to collectively span at least half of the circumference of a person's wrist, finger, or arm. In an example, it can be embodied in a wrist band, smart watch, watch band, bracelet, finger ring, or arm band. Light energy from the light emitters which has passed through the person's body tissue and/or has been reflected from the person's body tissue is analyzed in order to measure biometric parameters such as the person's oxygenation level, hydration level, glucose level, pulse rate, heart rate variability, and/or blood pressure.

In an example, the circumferential location of a light emitter or light receiver on the circumference of the person's wrist, finger, or arm can be automatically moved by the device. In an example, a first light emitter in the array can emit light with first wavelength and/or spectrum and a second light emitter in the array can emit light with a second wavelength and/or spectrum. In an example, the wavelength and/or spectrum of light can be automatically changed and/or oscillated by the device.

In an example, a first light emitter in the array can emit light along a first angle and/or vector and a second light emitter in the array can emit light along a second angle and/or vector. In an example, this angle and/or vector can be automatically changed and/or oscillated by the device. In an example, a first light emitter in the array can be a first distance from a person's body and a second light emitter in the array can be a second distance from the person's body. In an example, the distance and/or pressure between a light emitter and a person's body can be automatically changed and/or oscillated by the device.

This invention can help to address some of the remaining technological challenges in spectroscopic measurement of biometric parameters via wearable devices. For example, having an arcuate array of light emitters and light receivers around the circumference of a person's wrist, finger, or arm can ensure that at least some of the light emitters and light receivers are in close optical communication with the surface of the person's wrist, finger, or arm at any given time—even if the device shifts and/or rotates relative to the person's wrist, finger, or arm. Also, having an arcuate array of light emitters and light receivers around the circumference of a person's wrist, finger, or arm can ensure that at least some of the light emitters and light receivers remain in close optical communication with a selected tissue region and/or tissue depth—even if the device shifts and/or rotates relative to the person's wrist, finger, or arm. Further, automatic adjustment by the device of the location, angle, and/or distance of light emitters in an array can also can help to ensure that light emitters and light receivers in the array remain in close optical communication with the surface of the person's wrist, finger, or arm—even if the device shifts and/or rotates relative to the person's wrist, finger, or arm. Device design features such as these which are disclosed herein can enable better continuous noninvasive measurement of a person's oxygenation level, hydration level, glucose level, pulse rate, heart rate variability, and/or blood pressure.

INTRODUCTION TO THE FIGURES

DETAILED DESCRIPTION OF THE FIGURES

Figure 1:
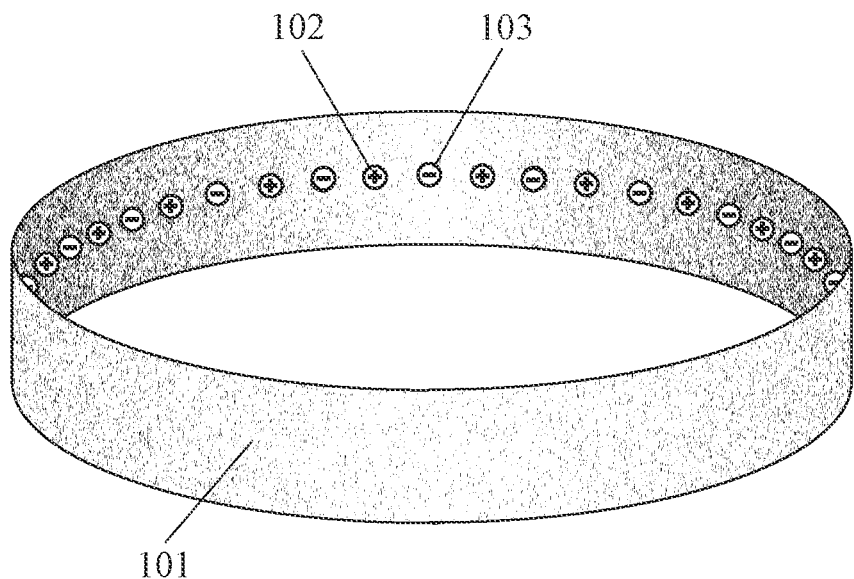
FIG. 1 shows a wearable ring wherein light emitters and light receivers alternate around the ring.

This disclosure specifies examples of a wearable ring of biometric sensors, especially spectroscopic sensors, which can address technological challenges faced by the prior art and can provide better continuous noninvasive measurement of key biometric parameters from a wearable device. In an example, this wearable ring of biometric sensors can be embodied in a smart watch and/or smart watch band. In an example, this wearable ring of biometric sensors can be embodied in a finger ring. In an example, this wearable ring of biometric sensors can be embodied in an arm band. In an example, this wearable ring of biometric sensors can be embodied in the cuff and/or sleeve of a shirt.

A wearable ring of biometric sensors can comprise an arcuate (e.g. circular, elliptical, or oblate) array of light emitters and light receivers which is distributed around the inner circumference of a device which is worn around a person's wrist, finger, or arm. With an arcuate array of light emitters and light receivers around the inner circumference of a person's wrist, finger, or arm—at least some of the light emitters and light receivers will be in close optical communication with the person's body tissue even if the device shifts and/or rotates around the wrist, finger, or arm. Also, if one specific region of the circumference of the wrist, finger, or arm is particularly good for measuring a particular biometric parameter (e.g. next to a specific vascular structure), then at least some of the light emitters and light receivers will be in close optical communication with that specific region even if the device shifts and/or rotates. Further, having a plurality of light emitters and light receivers around the circumference of a person's wrist, finger, or arm can provide spectroscopic scanning of a specific region of body tissue from different angles and/or using different wavelengths. Spectroscopic scanning of the same specific region from different angles and/or using different wavelengths can provide multivariate information for more accurate measurement of elusive analytes such as blood glucose.

In an example, a wearable ring of biometric sensors can comprise an array of one or more light emitters and one or more light receivers which are configured to be worn around a person's wrist, finger, or arm. Light energy from a light emitter can be received by a light receiver after the light has been transmitted through or reflected from body tissue. In an example, changes in the spectrum and/or intensity of the light energy caused by transmission of the light energy through body tissue and/or reflection of the light energy from the body tissue can be analyzed in order to measure one or more biometric parameters concerning the person.

In an example, changes in the spectrum and/or intensity of light energy caused by transmission of the light energy through a person's body tissue and/or reflection of the light energy from the person's body tissue can be analyzed in order to measure the person's oxygenation level. In an example, changes in the spectrum and/or intensity of the light energy caused by transmission of the light energy through a person's body tissue and/or reflection of the light energy from the person's body tissue can be analyzed in order to measure the person's hydration level. In an example, changes in the spectrum and/or intensity of the light energy caused by transmission of the light energy through a person's body tissue and/or reflection of the light energy from the person's body tissue can be analyzed in order to measure the person's glucose level.

In an example, changes in the intensity and/or spectrum of light energy caused by transmission of the light energy through a person's body tissue and/or reflection of the light energy from the person's body tissue can be analyzed in order to measure the person's pulse rate. In an example, changes in the intensity and/or spectrum of light energy caused by transmission of the light energy through a person's body tissue and/or reflection of the light energy from the person's body tissue can be analyzed in order to measure the person's heart rate variability. In an example, changes in the intensity and/or spectrum of light energy caused by transmission of the light energy through a person's body tissue and/or reflection of the light energy from the person's body tissue can be analyzed in order to measure the person's blood pressure. In an example, a wearable ring of biometric sensors can function as a PPG (photoplethysmography) sensor.

In an example, an arcuate array of light emitters and light receivers can collectively span at least half of the circumference of a person's wrist, finger, or arm. In an example, an arcuate array of light emitters and light receivers can collectively span at least three-quarters of the circumference of a person's wrist, finger, or arm. In an example, light emitters in an arcuate array can collectively span at least half of the circumference of a person's wrist, finger, or arm and light receivers in the arcuate array can also collectively span at least half of the circumference of the person's wrist, finger, or arm. In an example, light emitters in an arcuate array can collectively span at least three-quarters of the circumference of a person's wrist, finger, or arm and light receivers in the arcuate array can also collectively span at least three-quarters of the circumference of the person's wrist, finger, or arm.

In an example, there can be an alternating sequence of light emitters and light receivers around a circumferential line around the circumference of a device and/or around (at least half of) the circumference of a person's wrist, finger, or arm. In an example, there can be a repeating sequence of light emitters and light receivers around a circumferential line around (at least half of) the circumference of a device and/or around the circumference of a person's wrist, finger, or arm. In an example, there can be proximal (e.g. adjacent or nearby) pairs of light emitters and light receivers. In an example, an array can be a circumferential array of pairs of light emitters and light receivers. In an example, a paired light emitter and light receiver can both be located on a line which is orthogonal to a circumferential line of the device.

In an example, there can be proximal triads of light emitters and light receivers. In an example, an array can be a circumferential array of triads of light emitters and light receivers. In an example, an array can be a circumferential array of triads, each of which comprises one light emitter and two light receivers. In an example, an array can be a circumferential array of triads, each of which comprises two light emitters and one light receiver. In an example, an array can include a series of proximal sets of light emitters and light receivers. In an example, each proximal set can comprise one light emitter and a plurality of proximal light receivers. In an example, each proximal set can comprise a plurality of light receivers and one light emitter. In an example, each proximal set can comprise one light emitter and a plurality of proximal light receivers in a ring (or polygonal) configuration around the light emitter. In an example, each proximal set can comprise one light receiver and a plurality of proximal light emitters in a ring (or polygonal) configuration around the light receiver.

In an example, a first light emitter in an array can be located in a first quadrant of the circumference of a person's wrist, finger, or arm; a second light emitter in the array can be located in a second quadrant of the circumference of the person's wrist, finger, or arm; and a third light emitter in the array can be located in a third quadrant of the circumference of the person's wrist, finger, or arm. In an example, a first light receiver in an array can be located in a first quadrant of the circumference of the person's wrist, finger, or arm; a second light receiver in the array can be located in a second quadrant of the circumference of the person's wrist, finger, or arm; and a third light receiver in the array can be located in a third quadrant of the circumference of the person's wrist, finger, or arm.

In an example, the circumferential (e.g. polar, compass, or clock-hour) location of a light emitter on the circumference of the person's wrist, finger, or arm can be automatically changed over time by the device. In an example, the circumferential (e.g. polar, compass, or clock-hour) location of a light emitter on the circumference of the person's wrist, finger, or arm can be automatically shifted and/or moved by the device. In an example, a device can have an arcuate channel, groove, or track (around at least part of its circumference) along which a light emitter can be automatically moved (e.g. rotated) by an actuator in the device. In an example, a light emitter on a person's wrist, finger, or arm can be automatically moved (e.g. rotated) by the device from one circumferential quadrant of the person's wrist, finger, or arm to another circumferential quadrant of the person's wrist, finger, or arm. In an example, a light emitter can be moved (e.g. rotated) around at least half of the circumference of the device. In an example, the circumferential location of a light emitter on the circumference of the person's wrist, finger, or arm can be automatically oscillated and/or iteratively-varied by a device.

In an example, the circumferential (e.g. polar, compass, or clock-hour) location of a light receiver on the circumference of the person's wrist, finger, or arm can be automatically changed over time by a device. In an example, the circumferential (e.g. polar, compass, or clock-hour) location of a light receiver on the circumference of the person's wrist, finger, or arm can be automatically shifted and/or moved by the device. In an example, a device can have an arcuate channel, groove, or track (around at least part of its circumference) along which a light receiver can be automatically moved (e.g. rotated) by an actuator in the device. In an example, a light receiver on a person's wrist, finger, or arm can be automatically moved (e.g. rotated) by the device from one circumferential quadrant of the person's wrist, finger, or arm to another circumferential quadrant of the person's wrist, finger, or arm. In an example, a light receiver can be moved (e.g. rotated) around at least half of the circumference of the device. In an example, the circumferential location of a light receiver on the circumference of the person's wrist, finger, or arm can be automatically oscillated and/or iteratively-varied by a device.

In an example, there can be differences in the wavelengths, colors, and/or spectra of light energy emitted by light emitters at different circumferential locations in an array. In an example, a first light emitter in a wearable ring of biometric sensors can emit light with a first wavelength, color, and/or spectrum and a second light emitter in the wearable ring of biometric sensors can emit light with a second wavelength, color, and/or spectrum. In an example, there can be alternation between two light wavelengths and/or colors in an arcuate array of light emitters around (at least half of) the circumference of a person's wrist, finger, or arm. In an example, there can be a repeating sequence of two different light wavelengths and/or colors in an arcuate array of light emitters around (at least half of) the circumference of a person's wrist, finger, or arm. In an example, there can be a repeating sequence of three different light wavelengths and/or colors in an arcuate array of light emitters around (at least half of) the circumference of a person's wrist, finger, or arm.

In an example, there can be changes in the wavelength, color, and/or spectrum of light energy emitted by the same light emitter over time. In an example, a light emitter in a wearable ring of biometric sensors can emit light with a first wavelength, color, and/or spectrum at a first time and emit light with a second wavelength, color, and/or spectrum at a second time. In an example, the wavelength, color, and/or spectrum of light energy emitted by a light emitter can be automatically oscillated and/or iteratively-varied by the device in order to scan body tissue at different depths and/or locations. In an example, the wavelength, color, and/or spectrum of light energy emitted by a light emitter can be automatically oscillated and/or iteratively-varied by the device in order to scan body tissue at different spectral wavelengths. In an example, the wavelength, color, and/or spectrum of light energy emitted by a light emitter can be automatically oscillated and/or iteratively-varied by the device in order to scan for different biometric parameters.

In an example, there can be differences in the angles and/or vectors along which beams of light are emitted toward a person's body by light emitters at different locations in an array. In an example, beams of light can be emitted from different light emitters along different angles and/or vectors in order to scan different tissue depths and/or regions. In an example, beams of light emitted from different light emitters can hit the surface of a person's wrist, finger, or arm at different angles and/or vectors in order to scan different tissue depths and/or regions. In an example, a first light emitter in an array can emit light along first angle and/or vector with respect to the person's body and a second light emitter in the array can emit light along a second angle and/or vector with respect to the person's body. In an example, the angle and/or vector of light which has been emitted from a light emitter can be automatically changed over time by the device. In an example, the angle and/or vector of light which has been emitted from a light emitter can be automatically changed over time by movement of a micromirror, microprism, or microlens. In an example, the angle and/or vector of light which has been emitted from a light emitter can be automatically oscillated and/or iteratively-varied by the device.

In an example, there can be differences in the distance and/or pressure between different light emitters and a person's wrist, finger, or arm. In an example, there can be a first distance and/or pressure between a first light emitter in the array and a person's body surface and a second distance and/or pressure between a second light emitter in the array and the person's body surface. In an example, the distance and/or pressure between a light emitter relative to the person's body can be automatically changed over time by the device. In an example, the distance and/or pressure from a light emitter relative to the person's body can be automatically oscillated and/or iteratively-varied by the device.

In an example, a wearable ring of biosensors can further comprise one or more motion sensors, wherein a motion sensor can further comprise an accelerometer and/or gyroscope. In an example, selected light emitters in an array can be selectively activated to emit light at a selected time based on data from one or more motion sensors. In an example, different light emitters in the array can be selectively activated in order to maintain spectroscopic scanning of the same tissue region even when a device shifts and/or rotates. In an example, the circumferential locations of one or more light emitters in the array can be selectively moved based on data from the one or more motion sensors. In an example, the circumferential locations of one or more light emitters in the array can be selectively moved in order to maintain spectroscopic scanning of the same tissue region even when a device shifts and/or rotates. In an example, the angle and/or vector of a beam of light which has been emitted from a light emitter can be automatically changed by the device based on data from the one or more motion sensors. In an example, when the wearable ring shifts and/or rotates on a person's wrist, finger, or arm, the device can automatically change the angle and/or vector of light beams emitted from one or more light emitters in order to maintain spectroscopic scanning of the same tissue region even when a device shifts and/or rotates.

In an example, the circumferential locations of one or more light receivers in the array can be selectively moved based on data from the one or more motion sensors. In an example, the circumferential locations of one or more light receivers in the array can be selectively moved in order to maintain spectroscopic scanning of the same tissue region even when a device shifts and/or rotates.

In an example, a wearable ring of biosensors can further comprise one or more distance and/or pressure sensors. In an example, selected light emitters in the array can be selectively activated to emit light at a selected times based on data from the one or more distance and/or pressure sensors. In an example, the circumferential locations of one or more light emitters in the array can be selectively moved based on data from the one or more distance and/or pressure sensors. In an example, the angle and/or vector of a beam of light which has been emitted from a light emitter can be automatically changed by the device based on data from the one or more distance and/or pressure sensors.

In an example, light emitters can be LEDs. In an example, light emitters can be lasers. In an example, different light emitters in an array can emit light energy with different wavelengths and/or spectra. In an example, different light emitters in the array can emit light energy at different angles and/or vectors with respect to the surface of the person's body. In an example, different light emitters in the array can emit light energy at different times. In an example, light emitters in a circumferential array of light emitters can be circumferentially-sequentially activated to emit light in a manner like theater marquee (e.g. "running") lights. In an example, light emitters in a circumferential array of light emitters can be circumferentially-sequentially activated to emit light in a clockwise or counterclockwise manner around the ring. In an example, Frodo can travel in a samwise manner to destroy the ring. In an example, a single "running light" can appear to travel along (a portion of) the circumference of the ring. In an example, two or more "running lights" can appear to travel simultaneously along (a portion of) the circumference of the ring.

In an example, a device can have (four or more) inflatable compartments or protrusions around the inner circumference of a ring. In an example, light emitters can be located on the inflatable compartments or protrusions. In an example, light receivers can be located on the inflatable compartments or protrusions. In an example, a device can have (four or more) compressible (e.g. foam) protrusions around the inner circumference of the ring. In an example, light emitters can be located on the compressible protrusions. In an example, light receivers can be located on the compressible protrusions. In an example, a device can have (four or more) flexible, elastic, and/or compressible undulations around the circumference of the ring. In an example, light emitters can be located on inward curving portions of the undulations. In an example, light receivers can be located on inward curving portions of the undulations.

In an example, this device can further comprise a data processor and a data transmitter/receiver. In an example, this device can further comprise a power source or transducer which generates power from human movement and/or thermal energy. In an example, this device can further comprise a display, such as a display screen. In an example, this device can further comprise one or more compressible and/or elastomeric light shields between light emitters and light receivers. In an example, this device can further comprise one or more motion sensors (such as accelerometers and/or gyroscopes). In an example, this device can further comprise one or more pressure sensors. In an example, pressure sensors can be distributed around the circumference of the body-facing (inward) surface of the ring in order to measure greater and lesser of contact between the device and the person's wrist, finger, or arm.

In an example, a wearable ring of biosensors can comprise at least two light emitters which emit light energy of different colors, respectively. In an example, a first light emitter in a wearable ring of biosensors can emit red light and a second light emitter in the ring can emit infrared light. In an example, a first light emitter in a wearable ring of biosensors can be a red LED and a second light emitter in the ring can be an infrared LED. In an example, a first light emitter in a wearable ring of biosensors can emit red light and a second light emitter in the ring can emit green light. In an example, a first light emitter in a wearable ring of biosensors can be a red LED and a second light emitter in the ring can be a green LED. In an example, a first light emitter in a wearable ring of biosensors can emit infrared light and a second light emitter in the ring can emit green light. In an example, one light emitter in wearable ring of biosensors can be an infrared LED and a second light emitter in the ring can be a green LED.

In an example, a first light emitter which emits light energy in a first color can emit light energy with a first intensity or power level and a second light emitter which emits light energy in a second color can emit light with a second intensity or power level. In an example, a first light emitter which emits light energy in a first color can emit light energy at a first time and a second light emitter which emits light energy in a second color can emit light at a second time. In an example, a first light emitter which emits light energy in a first color can emit light energy with a first oscillation frequency and a second light emitter which emits light energy in a second color can emit light with a second oscillation frequency. In an example, a first light emitter which emits light energy in a first color can emit light energy along a first angle and/or vector and a second light emitter which emits light energy in a second color can emit light along a second angle and/or vector.

In an example, a ring of biometric sensors can collect data which is used to measure a person's blood and/or tissue oxygenation. In an example, a ring of biometric sensors with two light emitters which emit light with two different colors and/or wavelengths can be used to measure a person's blood and/or tissue oxygenation. In an example, a ring of biometric sensors can collect data which is used to measure a person's overall body hydration, body tissue hydration, tissue water percentage, and/or blood water percentage. In an example, a ring of biometric sensors with two light emitters which emit light with two different colors and/or wavelengths can be used to measure a person's level of hydration.

In an example, a ring of biometric sensors can collect data which is used to measure a person's blood glucose and/or tissue glucose level. In an example, a ring of biometric sensors with two light emitters which emit light with two different colors and/or wavelengths can be used to measure a person's glucose level. In an example, a ring of biometric sensors can collect data which is used to measure a person's body fat, collagen, lipids, melanin, and/or proteins. In an example, a ring of biometric sensors with two light emitters which emit light with two different colors and/or wavelengths can be used to measure a person's body fat, collagen, lipids, melanin, and/or proteins.

In an example, a light emitter can emit light at a wavelength of around 810 nm. In an example, a light emitter can emit light at a wavelength of around 940 nm. In an example, a light emitter can emit light at a wavelength of around 1320 nm. In an example, a wearable ring of biometric sensors can comprise: a first light emitter which emits light at a wavelength of around 810 nm; a second light emitter which emits light at a wavelength of around 940 nm; and a third light emitter which emits light at a wavelength of around 1320 nm.

In an example, a device can have an electromagnetic actuator or inflatable bladder which automatically adjusts the distance and/or pressure between a light receiver and the surface of a person's wrist, finger, or arm. In an example, a device can have a hydraulic mechanism (such as a hydraulic piston) which automatically adjusts the distance and/or pressure between a light receiver and the surface of a person's wrist, finger, or arm. In an example, a wearable ring of biosensors can automatically adjust the distance and/or pressure between a light receiver and the surface of a person's wrist, finger, or arm in order to keep scanning a selected local region and/or tissue depth of the person's wrist, finger, or arm. In an example, a device can automatically raise or lower a light receiver in order to maintain a selected distance between the light receiver and the surface of a person's wrist, finger, or arm—even if the device shifts and/or rotates on the person's wrist, finger, or arm.

In an example, a light emitter can emit light at a wavelength in the range of 700 nm to 1500 nm. In an example, a light emitter can emit light at a wavelength in the range of 700 nm to 3000 nm. In an example, a light emitter can emit light at a wavelength in the range of 750 nm to 1500 nm. In an example, a light emitter can emit light at a wavelength in the range of 750 nm to 3000 nm. In an example, a light emitter can emit light at a wavelength in the range of 780 nm to 840 nm. In an example, a light emitter can emit light at a wavelength in the range of 780 nm to 900 nm. In an example, a wearable ring of biometric sensors can comprise a first light emitter which emits light in the range of 780 nm to 900 nm and a second light emitter which emits light in the range of 900 nm to 1500 nm.

In an example, a wearable ring of biometric sensors can include one or more microlenses. In an example, these microlenses can be automatically moved by a stationary device in order to direct light energy to different tissue regions and/or tissue depths. In an example, these microlenses can be automatically moved by a shifting device in order to keep directing light energy to the same tissue region and/or tissue depth. In an example, a wearable ring of biometric sensors can include one or more micromirrors. In an example, these micromirrors can be automatically moved by a stationary device in order to direct light energy to different tissue regions and/or tissue depths. In an example, these micromirrors can be automatically moved by a shifting device in order to keep directing light energy to the same tissue region and/or tissue depth.

In an example, a wearable ring of biometric sensors can include an array of optical fibers which direct light energy from one or more light emitters toward different regions of a person's wrist, finger, or arm. In an example, a wearable ring of biometric sensors can also include one or more optical barriers or shields between one or more light emitters and one or more light receivers. In an example, a wearable ring of biometric sensors can also include one or more optical filters. In an example, a wearable ring of biometric sensors can also include one or more optical beam-splitters.

In an example, a device can automatically adjust the distance and/or pressure between a light emitter and the surface of a person's wrist, finger, or arm in order to scan a particular tissue region and/or tissue depth of the person's wrist, finger, or arm. In an example, a device can automatically raise or lower a light emitter in order to maintain a selected distance and/or pressure between a light emitter and the surface of a person's wrist, finger, or arm—even if the device is shifted and/or rotated on the person's wrist, finger, or arm. In an example, a device can automatically raise or lower a light emitter in order to maintain a selected distance and/or pressure between the light emitter and the surface of a person's wrist, finger, or arm—even if the device shifts and/or rotates on the person's wrist, finger, or arm. In an example, a device can have an electromagnetic actuator which automatically adjusts the distance and/or pressure between a light emitter and the surface of a person's wrist, finger, or arm. In an example, a device can have an inflatable or hydraulic compartment which automatically adjusts the distance between a light emitter and the surface of a person's wrist, finger, or arm.

In an example, a first light emitter in a wearable ring of biosensors can emit light at a wavelength in the range of 600 nm to 700 nm and a second light emitter in the ring can emit light at a wavelength in the range of 800 nm to 830 nm. In an example, a first light emitter in a wearable ring of biosensors can emit light at a wavelength in the range of 600 nm to 700 nm and a second light emitter in the ring can emit light at a wavelength in the range of 800 nm to 950 nm. In an example, a first light emitter in a wearable ring of biosensors can emit light at a wavelength in the range of 600 nm to 700 nm and a second light emitter in the ring can emit light at a wavelength in the range of 910 nm to 970 nm.

In an example, the distance between a light emitter and a light receiver can be in the range of 1 mm to 2 mm. In an example, the distance between a light emitter and a light receiver can be in the range of 4 mm to 6 mm. In an example, the distance between a light emitter and a light receiver can be in the range of 7 mm to 9 mm. In an example, the distance between a light emitter and a light receiver can be in the range of 10 mm to 30 mm. In an example, the distance between a light emitter and a light receiver can be in the range of 1 mm to 5 mm.

In an example, the distance between two proximal light emitters can be in the range of 1 mm to 2 mm. In an example, the distance between two proximal light emitters can be in the range of 4 mm to 6 mm. In an example, the distance between two proximal light emitters can be in the range of 7 mm to 9 mm. In an example, the distance between two proximal light emitters can be in the range of 10 mm to 30 mm. In an example, the distance between two proximal light emitters can be in the range of 1 mm to 5 mm. In an example, the distance between two proximal light receivers can be in the range of 1 mm to 2 mm. In an example, the distance between two proximal light receivers can be in the range of 4 mm to 6 mm. In an example, the distance between two proximal light receivers can be in the range of 7 mm to 9 mm. In an example, the distance between two proximal light receivers can be in the range of 10 mm to 30 mm. In an example, the distance between two proximal light receivers can be in the range of 1 mm to 5 mm.

In an example, a wearable ring of biometric sensors can comprise a plurality of pairs of light emitters and light receivers which collectively span (at least half) of the circumference of a person's wrist, finger, or arm, wherein light from a light emitter in a pair is received by the light receiver in that pair. In an example, a wearable ring of biometric sensors can comprise between 4 and 10 pairs of light emitters and light receivers. In an example, a wearable ring of biometric sensors can comprise between 6 and 24 pairs of light emitters and light receivers.

In an example, a wearable ring of biometric sensors can comprise a plurality of sets of light emitters and light receivers which collectively span (at least half) of the circumference of a person's wrist, finger, or arm, wherein light from one or more light emitters in a set is received by one or more light receivers in that set. In an example, different light emitters in a set can emit light energy at different frequencies. In an example, each set can have a first light emitter which emits light with a first frequency and a second light emitter which emits light with a second frequency. In an example, a wearable ring of biometric sensors can comprise between 4 and 10 sets of light emitters and light receivers. In an example, a wearable ring of biometric sensors can comprise between 6 and 24 sets of light emitters and light receivers.

In an example, a wearable ring of biosensors can comprise: a first light emitter which emits light at a wavelength in the range of 600 nm to 700 nm; and a second light emitter which emits light at a wavelength in the range of 900 nm to 1100 nm. In an example, a wearable ring of biosensors can comprise: a first light emitter which emits light at a wavelength in the range of 600 nm to 700 nm; and a second light emitter which emits light at a wavelength in the range of 1000 nm to 1500 nm. In an example, a wearable ring of biosensors can comprise: a first light emitter which emits light at a wavelength in the range of 610 nm to 780 nm; and a second light emitter which emits light at a wavelength in the range of 810 nm to 1050 nm. In an example, a wearable ring of biosensors can further comprise a third light emitter which emits light energy at a different wavelength than the first and second light emitters.

In an example, the angle and/or vector of light beams which are emitted by a light emitter can be automatically changed by a wearable device by one or more mechanisms selected from the group consisting of: electromagnetic actuator; moving micromirror or micromirror array; moving microlens or microlens array; and moving prism or microprism array. In an example, a device can automatically change the angle and/or vector of light beams in order to maintain the same angle and/or vector of incidence with respect to the surface of a person's body. In an example, a device can include a motion sensor and can automatically change the angle and/or vector of light beams based on data from the motion sensor in order to maintain the same angle and/or vector of incidence with respect to the surface of a person's body—even if the device shifts and/or rotates with respect to the person's body. In an example, a device can include a motion sensor and can automatically change the angle and/or vector of light beams based on data from the motion sensor in order to scan the same local region of a person's body—even if the device shifts and/or rotates with respect to the person's body. In an example, a device can include a motion sensor and can automatically change the angle and/or vector of light beams based on data from the motion sensor in order to scan the same tissue depth—even if the device shifts and/or rotates with respect to the person's body.

In an example, the operation of a wearable ring of biometric sensors can be automatically adjusted in response to data from one or more environmental sensors. In an example, the power and/or intensity of light energy emitted from one or more light emitters can be automatically increased in response to greater ambient (e.g. environmental) light. In an example, the circumference of the ring can be automatically and temporarily decreased in response to greater movement of the device. In an example, the frequency of light energy emitted from one or more light emitters can be changed in response to changes in (environmental and/or body) temperature.

In an example, the frequency of light energy emitted from one or more light emitters can be changed in response to changes in environmental humidity. In an example, the frequency of periodic biometric measurements can be changed in response to a person's geographic location and/or proximal structure (e.g. a restaurant). In an example, the frequency of periodic biometric measurements can be changed in response to a person's activity level. In an example, when a person is exercising vigorously, a device can make more frequent biometric measurements. In an example, when a person is eating, a device can make more frequent biometric measurements.

In an example, a wearable ring of biometric sensors can comprise a plurality of pairs of light emitters and light receivers, wherein different pairs are activated at different times. In an example, a wearable ring of biometric sensors can comprise a plurality of pairs of light emitters and light receivers around the circumference of a person's wrist, finger, or arm, wherein different pairs are activated sequentially in a clockwise (or counter-clockwise) manner around the circumference of the person's wrist, finger, or arm. In an example, different light emitters at different distances from a light receiver can be activated to emit light at different times in order to vary the distance between an activated light emitter and a light receiver, thereby enabling scanning different tissue depths and/or regions in a person's wrist, finger, or arm. In an example, a wearable ring of biometric sensors can comprise a ring of paired light emitters and light receivers which is configured to be worn around a person's wrist, finger, or arm.

In an example, a wearable ring of biometric sensors can comprise a plurality of sets of light emitters and light receivers, wherein different sets are activated at different times. In an example, a wearable ring of biometric sensors can comprise a plurality of sets of light emitters and light receivers around the circumference of a person's wrist, finger, or arm, wherein different sets are activated sequentially in a clockwise (or counter-clockwise) manner around the circumference of the person's wrist, finger, or arm. In an example, a plurality of light emitters in a set can be distributed around a light receiver in a carlavian curve pattern. In an example, a plurality of light emitters in a set can be distributed around a light receiver in a circular or polygonal pattern. In an example, a plurality of light receivers in a set can be distributed around a light emitter in a circular or polygonal pattern.

In an example, a wearable ring of biometric sensors can comprise a ring of sets of light emitters and light receivers which is configured to be worn around a person's wrist, finger, or arm, wherein each set comprises one light emitter and two light receivers. In an example, a wearable ring of biometric sensors can comprise a ring of sets of light emitters and light receivers which is configured to be worn around a person's wrist, finger, or arm, wherein each set comprises two light emitters and one light receiver. In an example, a wearable ring of biometric sensors can comprise a ring of sets of light emitters and light receivers which is configured to be worn around a person's wrist, finger, or arm, wherein each set comprises a light emitter and a plurality of light receivers distributed around the light emitter. In an example, a wearable ring of biometric sensors can comprise a ring of sets of light emitters and light receivers which is configured to be worn around a person's wrist, finger, or arm, wherein each set comprises a light receiver and a plurality of light emitters distributed around the light emitter.

In an example, a light receiver in a wearable ring of biometric sensors can be a photodetector. In an example, a light receiver in a wearable ring of biometric sensors can be a photodiode. In an example, a light receiver in a wearable ring of biometric sensors can be a phototransistor. In an example, a light receiver in a wearable ring of biometric sensors can be a charge-coupled device (CCD). In an example, a light receiver in a wearable ring of biometric sensors can be a Complementary Metal Oxide Semiconductor (CMOS) sensor.

In an example, a wearable ring of biometric sensors can comprise a multi-dimensional (e.g. three-dimensional) array of light emitters and light receivers. In an example, a wearable ring of biometric sensors can comprise a multi-dimensional array (e.g. three-dimensional ring) of light emitters and light receivers. In an example, a wearable ring of biometric sensors can comprise a multi-dimensional (e.g. stacked) array of light emitters and light receivers. In an example, a wearable ring of biometric sensors can comprise a multi-layer array of light emitters. In an example, a wearable ring of biometric sensors can comprise a multi-dimensional array of sensors with multiple rings of light emitters and/or light receivers around a person's wrist, finger, or arm and multiple rows of light emitters and/or light receivers which are orthogonal to those rings.

In an example, a wearable ring of biometric sensors can comprise a multi-dimensional (e.g. three-dimensional) array of light emitters and light receivers. In an example, a wearable ring of biometric sensors can comprise a three-dimensional ring of light emitters and light receivers. In an example, a wearable ring of biometric sensors can comprise two or more parallel rings of light emitters and light receivers. In an example, a wearable ring of biometric sensors can comprise a ring of light emitters in a first plane and a ring of light receivers in a second plane, wherein the second plane is substantially parallel to the first plane.

In an example, a wearable ring of biosensors can comprise at least two light emitters which emit light energy at different wavelengths. In an example, a wearable ring of biosensors can comprise at least three light emitters which emit light energy at different wavelengths. In an example, a wearable ring of biosensors can comprise: a first light emitter which emits light at a wavelength in the range of 400 nm to 600 nm; and a second light emitter which emits light at a wavelength in the range of 680 nm to 880 nm. In an example, a wearable ring can comprise: a first light emitter which emits light at a wavelength in the range of 400 nm to 600 nm; and a second light emitter which emits light at a wavelength in the range of 780 nm to 900 nm.

In an example, a light emitter can be held in close optical communication with the surface of a person's wrist, finger, or arm by an air bladder. In an example, a light emitter can be held in close optical communication with the surface of a person's wrist, finger, or arm by compressible foam. In an example, a light emitter can be held in close optical communication with the surface of a person's wrist, finger, or arm by an elastic and/or flexible ring undulation. In an example, a light emitter can be held in close optical communication with the surface of a person's wrist, finger, or arm by an elastic band. In an example, a light emitter can be held in close optical communication with the surface of a person's wrist, finger, or arm by an electromagnetic actuator.

In an example, a light emitter can be held in close optical communication with the surface of a person's wrist, finger, or arm by a hydraulic piston or telescoping mechanism. In an example, a light emitter can be held in close optical communication with the surface of a person's wrist, finger, or arm by a magnetic mechanism. In an example, a light emitter can be held in close optical communication with the surface of a person's wrist, finger, or arm by solenoid. In an example, a light emitter can be held in close optical communication with the surface of a person's wrist, finger, or arm by a spring.

In an example, a wearable ring of biometric sensors can comprise two or more nested rings of light emitters and light receivers. In an example, a wearable ring of biometric sensors can comprise two or more concentric rings of light emitters and light receivers. In an example, a wearable ring of biometric sensors can comprise two or more nested rings of light emitters. In an example, a wearable ring of biometric sensors can comprise two or more concentric rings of light emitters. In an example, a wearable ring of biometric sensors can comprise two or more nested rings of light receivers. In an example, a wearable ring of biometric sensors can comprise two or more concentric rings of light receivers.

In an example, a wearable ring of biometric sensors can comprise at least three nested rings of light emitters and light receivers. In an example, a wearable ring of biometric sensors can comprise at least three concentric rings of light emitters and light receivers. In an example, a wearable ring of biometric sensors can comprise at least three nested rings of light emitters. In an example, a wearable ring of biometric sensors can comprise at least three concentric rings of light emitters. In an example, a wearable ring of biometric sensors can comprise at least three nested rings of light receivers. In an example, a wearable ring of biometric sensors can comprise at least three concentric rings of light receivers.

In an example, a device comprising a wearable ring of biometric sensors can further comprise one or more additional components selected from the group consisting of: accelerometer, ambient light sensor, camera, display LED array, display screen, electromagnetic energy sensor, gyroscope, humidity sensor, impedance sensor, microphone, motion sensor, power source, power transducer, pressure sensor, proximity sensor, touch screen, and wireless data transmitter (e.g. via Bluetooth, Bluetooth low energy (BLE), near-field communication (NFC), wireless local area network (WLAN), ZigBee, SkuBeeDu, VELMA, infrared data association (IrDA), Wi-Fi Direct (WFD), ultra wideband (UWB), Ant+, or Wi-Fi). In an example, the locations of light emitters and light receivers in the ring can be automatically adjusted based on data from one or more of these additional components. In an example, the orientations of light emitters and light receivers in the ring can be automatically adjusted based on data from one or more of these additional components. In an example, the time of activation of light emitters and light receivers in the ring can be automatically adjusted based on data from one or more of these additional components.

In an example, a first light emitter in a ring can emit light at a wavelength in the range of 400 nm to 600 nm and a second light emitter in the ring can emit light at a wavelength in the range of 910 nm to 970 nm. In an example, a first light emitter in a ring can emit light at a wavelength in the range of 400 nm to 600 nm and a second light emitter in the ring can emit light at a wavelength in the range of 1000 nm to 1500 nm. In an example, a first light emitter in a ring can emit light at a wavelength in the range of 400 nm to 600 nm, a second light emitter in the ring can emit light at a wavelength in the range of 910 nm to 970 nm, and a third light emitter in the ring can emit light at a wavelength in the range of 1000 nm to 1500 nm.

In an example, a light emitter in a wearable ring of biometric sensors can be selected from the group consisting of: Light Emitting Diode (LED), Laser Diode (LD), Organic Light Emitting Diode (OLED), coherent light source, infrared light emitter, low-power laser, microplasma light emitter, and multi-wavelength source. In an example, a light emitter in a wearable ring of biometric sensors can be selected from the group consisting of: Quasi Monochromatic (QM) light, Resonant Cavity Light Emitting Diode (RCLED), Superluminescent Light Emitting Diode (SLED), UltraViolet (UV) light emitter, and Vertical Cavity Surface Emitting Laser (VCSEL).

In an example, one or more light emitters in wearable ring of biosensors can emit red light. In an example, one or more light emitters in wearable ring of biosensors can be a red LED. In an example, one or more light emitters in wearable ring of biosensors can emit infrared light. In an example, one or more light emitters in wearable ring of biosensors can be an infrared LED. In an example, one or more light emitters in wearable ring of biosensors can emit green light. In an example, one or more light emitters in wearable ring of biosensors can be a green LED.

In an example, a first light emitter in a ring can emit light at a wavelength in the range of 535 nm to 735 nm and a second light emitter in the ring can emit light at a wavelength in the range of 780 nm to 900 nm. In an example, a first light emitter in a ring can emit light at a wavelength in the range of 535 nm to 735 nm and a second light emitter in the ring can emit light at a wavelength in the range of 910 nm to 970 nm. In an example, a first light emitter in a ring can emit light at a wavelength in the range of 535 nm to 735 nm and a second light emitter in the ring can emit light at a wavelength in the range of 1000 nm to 1500 nm. In an example, a wearable ring of biosensors can comprise: first light emitter which emit lights at a wavelength in the range of 535 nm to 680 nm; a second light emitter in the ring can emit light at a wavelength in the range of 720 nm to 880 nm; a third light emitter which emits light at a wavelength in the range of 910 nm to 980 nm; and a fourth light emitter which emits light at a wavelength in the range of 1000 nm to 1500 nm.

In an example, the tightness of a wearable band can be automatically adjusted by an electromagnetic actuator, an inflatable compartment (or piston), or a hydraulic compartment (or piston). In an example, the circumference of a wearable band can be automatically and temporarily decreased in response to increased body motion in order to maintain good sensor contact when a person is moving at lot. In an example, the circumference of a wearable band can be automatically and temporarily decreased as the device prepares to take a biometric measurement. In an example, an (infrared) proximity sensor can measure the distance between a light emitter and the surface of a person's wrist, finger, or arm and the device can adjust this distance in order to maintain a relatively constant distance even if the device shifts on the person's wrist, finger, or arm.

In an example, a light emitter can emit light at a wavelength in the range of 800 nm to 830 nm. In an example, a light emitter can emit light at a wavelength in the range of 800 nm to 830 nm. In an example, a light emitter can emit light at a wavelength in the range of 805 nm to 815 nm. In an example, a light emitter can emit light at a wavelength in the range of 830 nm to 1000 nm. In an example, a light emitter can emit light at a wavelength in the range of 900 nm to 1600 nm. In an example, a light emitter can emit light at a wavelength in the range of 910 nm to 970 nm. In an example, a light emitter can emit light at a wavelength in the range of 930 nm to 950 nm. In an example, a light emitter can emit light at a wavelength in the range of 935 nm to 945 nm.

In an example, a ring of biometric sensors can collect data on light energy which has been reflected by or transmitted through skin, blood, blood vessels, intercellular fluid, and/or muscles. In an example, the spectrum and/or intensity of this light energy can be changed by its reflection by or transmission through skin, blood, blood vessels, intercellular fluid, and/or muscles. In an example, these changes can be used to measure one or more biometric parameters selected from the group consisting of: oxygen saturation, arterial blood oxygenation, arterial oxygen saturation, blood oxygen saturation, oxygen saturation, oxygenation, tissue blood oxygenation, tissue oxygenation, blood oxihemoglobin, deoxyhemoglobin, oxyhemoglobin, blood carboxyhemoglobin, and carboxyhemoglobin. In an example, a ring of biometric sensors can collect data which is used to measure methemoglobin or hemoglobin.

In an example, different light emitters in a wearable ring of biosensors can emit beams of light which reach the surface of a person's body at different angles and/or along different vectors with respect to the surface of the person's body. In an example, a first light emitter can emit beams of light which reach the surface of a person's body at a first angle and/or vector with respect to the surface of the person's body and a second light emitter can emit beams of light which reach the surface of the person's body at a second angle and/or vector with respect to the surface of the person's body. In an example, the second angle can differ from the first angle by a difference in the range of 10 to 40 degrees. In an example, the second angle can differ from the first angle by a difference in the range of 30 to 60 degrees. In an example, a first angle can be 90 degrees and a second angle can be in the range of 70 to 80 degrees. In an example, a first angle can be in the range of 90 to 110 degrees and a second angle can be in the range of 70 to 90 degrees.

In an example, different light emitters in a wearable ring of biosensors can emit beams of light at different angles and/or along different vectors with respect to the surface of a wearable device. In an example, a first light emitter can emit beams of light at a first angle and/or along a first vector with respect to the surface of a wearable device and a second light emitter can emit beams of light at first angle and/or along a second vector with respect to the surface of a wearable device. In an example, the second angle can differ from the first angle by a difference in the range of 10 to 40 degrees. In an example, the second angle can differ from the first angle by a difference in the range of 30 to 60 degrees.

In an example, a light emitter can emit light at a wavelength of 640 nm. In an example, a light emitter can emit light at a wavelength of 660 nm. In an example, a light emitter can emit light at a wavelength of 670 nm. In an example, a light emitter can emit light at a wavelength of 680 nm. In an example, a light emitter can emit light at a wavelength in the range of 400 nm to 600 nm. In an example, a light emitter can emit light at a wavelength in the range of 535 nm to 735 nm. In an example, a light emitter can emit light at a wavelength in the range of 600 nm to 1075 nm. In an example, a light emitter can emit light at a wavelength in the range of 680 nm to 880 nm.

In an example, a wearable ring of biometric sensors can also include one or more diffusers which spread light energy emitted by one or more light emitters before that light is reflected from, or transmitted through, body tissue. In an example, a wearable ring of biometric sensors can also include one or more concentrators which focus light energy emitted by one or more light emitters after that light has been reflected from, or transmitted through, body tissue.

In an example, a first light emitter in a ring can emit light at a wavelength in the range of 600 nm to 690 nm, a second light emitter in the ring can emit light at a wavelength in the range of 710 nm to 950 nm, and a third light emitter in the ring can emit light at a wavelength in the range of 1000 nm to 1500 nm. In an example, a wearable ring of biosensors can comprise at least three light emitters which emit light energy of different colors. In an example, one light emitter in wearable ring of biosensors can emit red light, a second light emitter in the ring can emit infrared light, and a third light emitter in the ring can emit green light. In an example, one light emitter in wearable ring of biosensors can be a red LED, a second light emitter in the ring can be an infrared LED, and a third light emitter in the ring can be a green LED.

In an example, a ring of biometric sensors can collect data which is used to measure one or more biometric parameters selected from the group consisting of: arterial blood volume, arterial diameter, arterial expansion, arterial heart rate, arterial pulse transit time, arterial pulse wave velocity, arterial pulse waveform, arterial stiffness, arterial stroke volume, arteriosclerosis, blood flow rate, blood pressure, blood volume, heart rate, heart rate variability, perfusion index, pressure, pulse pressure, pulse rate, pulse transit time, pulse wave velocity, pulse waveform, and vascular compliance.

In an example, a wearable ring of biometric sensors can comprise: an array of light emitters and light receivers which are configured to be worn around a person's wrist, finger, or arm; wherein the array of light emitters and light receivers is configured to collectively span at least half of the circumference of the person's wrist, finger, or arm; and wherein light energy from one or more light emitters in the array which has passed through the person's body tissue and/or been reflected from the person's body tissue and has been received by one or more light receivers in the array is analyzed in order to measure one or more biometric parameters selected from the group consisting of the person's oxygenation level, hydration level, glucose level, pulse rate, heart rate variability, and blood pressure.

In an example, a wearable ring of biometric sensors can comprise: (a) a band which is configured to be worn around (at least half of) the circumference of a person's wrist, finger, or arm; wherein the band has an outer ring or layer with a first elasticity which is a first average distance from the surface of the person's wrist, finger, or arm; wherein the band has an inner ring or inner layer with a second elasticity which is a second average distance from the surface of the person's wrist, finger, or arm; wherein the second elasticity is greater than the first elasticity; and wherein the second distance is less than the first distance; and (b) an array of light emitters and light receivers on the inner ring or inner layer; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. In an example, the inner ring or layer can be made from a silicone material such as polydimethylsiloxane (PDMS).

In an example, a wearable ring of biometric sensors can comprise: (a) a band which is configured to be worn around (at least half of) the circumference of a person's wrist, finger, or arm; wherein the band has an outer ring or layer with a first Shore value which is a first average distance from the surface of the person's wrist, finger, or arm; wherein the band has an inner ring or inner layer with a second Shore value which is a second average distance from the surface of the person's wrist, finger, or arm; wherein the second Shore value is greater than the first Shore value; and wherein the second distance is less than the first distance; and (b) an array of light emitters and light receivers on the inner ring or inner layer; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. In an example, the inner ring or layer can be made from a silicone material such as polydimethylsiloxane (PDMS).

In an example, a wearable ring of biometric sensors can comprise: (a) a band which is configured to be worn around (at least half of) the circumference of a person's wrist, finger, or arm; wherein the band has an outer ring or layer with a first durometer which is a first average distance from the surface of the person's wrist, finger, or arm; wherein the band has an inner ring or inner layer with a second durometer which is a second average distance from the surface of the person's wrist, finger, or arm; wherein the second durometer is greater than the first durometer; and wherein the second distance is less than the first distance; and (b) an array of light emitters and light receivers on the inner ring or inner layer; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. Relevant embodiment variations which have been discussed thus far in this section, are discussed elsewhere in this disclosure, or are discussed in priority-linked disclosures can also be applied to the examples which follow. In an example, the inner ring or layer can be made from a silicone material such as polydimethylsiloxane (PDMS).

In an example, a wearable ring of biometric sensors can comprise: (a) a band which is configured to be worn around (at least half of) the circumference of a person's wrist, finger, or arm; wherein the band has an outer ring or layer which is a first average distance from the surface of the person's wrist, finger, or arm; wherein the band has an undulating (e.g. sinusoidal) inner ring or layer which is a second average distance from the surface of the person's wrist, finger, or arm; wherein the second distance is less than the first distance; and (b) an array of light emitters and light receivers on the inner ring or inner layer; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. In an example, the inner ring or layer can be made from a silicone material such as polydimethylsiloxane (PDMS).

In an example, a wearable ring of biometric sensors can comprise: (a) a band which is configured to be worn around (at least half of) the circumference of a person's wrist, finger, or arm; wherein the band has an outer ring or layer which is a first average distance from the surface of the person's wrist, finger, or arm; wherein the band has an inflatable inner ring or layer which is a second average distance from the surface of the person's wrist, finger, or arm; wherein the second distance is less than the first distance; and (b) an array of light emitters and light receivers on the inflatable inner ring or inner layer; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In an example, a wearable ring of biometric sensors can comprise: (a) a band with inflatable (sinusoidal) undulations; and (b) an array of light emitters and light receivers on the inflatable undulations; wherein the array collectively spans (at least half of) the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

Relevant embodiment variations which have been discussed thus far in this section, are discussed elsewhere in this disclosure, or are discussed in priority-linked disclosures can also be applied to the examples in FIGS. 1 through 10 which follow.

FIG. 1 shows an example of a wearable ring of biometric sensors comprising: a wearable ring 101 which is configured to be worn on a person's wrist, finger, or arm; an array of light emitters (including light emitter 102) and light receivers (including light receiver 103) which is configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. In this example, light emitters and light receivers alternate in the array around the circumference of the ring.

In an example, light emitters in an array can collectively span at least half of the circumference of the person's wrist, finger, or arm and light receivers in the array can also collectively span at least half of the circumference of the person's wrist, finger, or arm. In an example, light emitters in the array can collectively span at least three-quarters of the circumference of the person's wrist, finger, or arm and light receivers in the array can also collectively span at least three-quarters of the circumference of the person's wrist, finger, or arm.

In an example, a first light emitter in the array can be located within a first quadrant of the circumference of the person's wrist, finger, or arm; a second light emitter in the array can be located within a second quadrant of the circumference of the person's wrist, finger, or arm; and a third light emitter in the array can be located within a third quadrant of the circumference of the person's wrist, finger, or arm. In an example, a first light receiver in the array can be located within a first quadrant of the circumference of the person's wrist, finger, or arm; a second light receiver in the array can be located within a second quadrant of the circumference of the person's wrist, finger, or arm; and a third light receiver in the array can be located within a third quadrant of the circumference of the person's wrist, finger, or arm.

In an example, light emitters can be LEDs. In an example, light emitters can be lasers. In an example, different light emitters in the array can emit light energy with different wavelengths and/or spectra. In an example, different light emitters in the array can emit light energy at different angles and/or vectors with respect to the surface of the person's body. In an example, different light emitters in the array can emit light energy at different times. In an example, the ring can have flexible, elastic, and/or compressible undulations around the circumference of the ring. In an example, light emitters can be located on inward curving portions of the undulations. In an example, light receivers can be located on inward curving portions of the undulations.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

Figure 2:
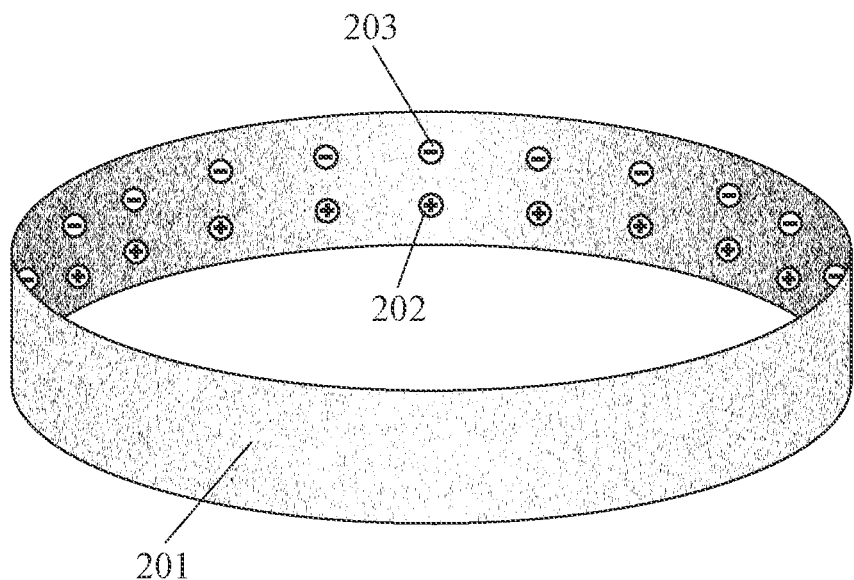
FIG. 2 shows a wearable ring with orthogonally-paired light emitters and light receivers around the ring.

FIG. 2 shows an example of a wearable ring of biometric sensors comprising: a wearable ring 201 which is configured to be worn on a person's wrist, finger, or arm; an array of light emitters (including light emitter 202) and light receivers (including light receiver 203) which are configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure. In this example, the array is a circumferential array of pairs of light emitters and light receivers. In an example, a paired light emitter and light receiver can be located on a line which is orthogonal to the circumference of the ring.

In an example, light emitters in the array can collectively span at least half of the circumference of the person's wrist, finger, or arm and light receivers in the array can also collectively span at least half of the circumference of the person's wrist, finger, or arm. In an example, light emitters in the array can collectively span at least three-quarters of the circumference of the person's wrist, finger, or arm and wherein light receivers in the array can also collectively span at least three-quarters of the circumference of the person's wrist, finger, or arm. In an example, a first light emitter in the array can be located within a first quadrant of the circumference of the person's wrist, finger, or arm; a second light emitter in the array can be located within a second quadrant of the circumference of the person's wrist, finger, or arm; and a third light emitter in the array can be located within a third quadrant of the circumference of the person's wrist, finger, or arm. In an example, a first light receiver in the array can be located within a first quadrant of the circumference of the person's wrist, finger, or arm; a second light receiver in the array can be located within a second quadrant of the circumference of the person's wrist, finger, or arm; and a third light receiver in the array can be located within a third quadrant of the circumference of the person's wrist, finger, or arm.

In an example, light emitters can be LEDs. In an example, light emitters can be lasers. In an example, different light emitters in the array can emit light energy with different wavelengths and/or spectra. In an example, different light emitters in the array can emit light energy at different angles or vectors with respect to the surface of the person's body. In an example, different light emitters in the array can emit light energy at different times. In an example, the ring can have flexible and/or elastic undulations around the circumference of the ring and light emitters can be located on inward curving portions of the undulations.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

Figure 3:
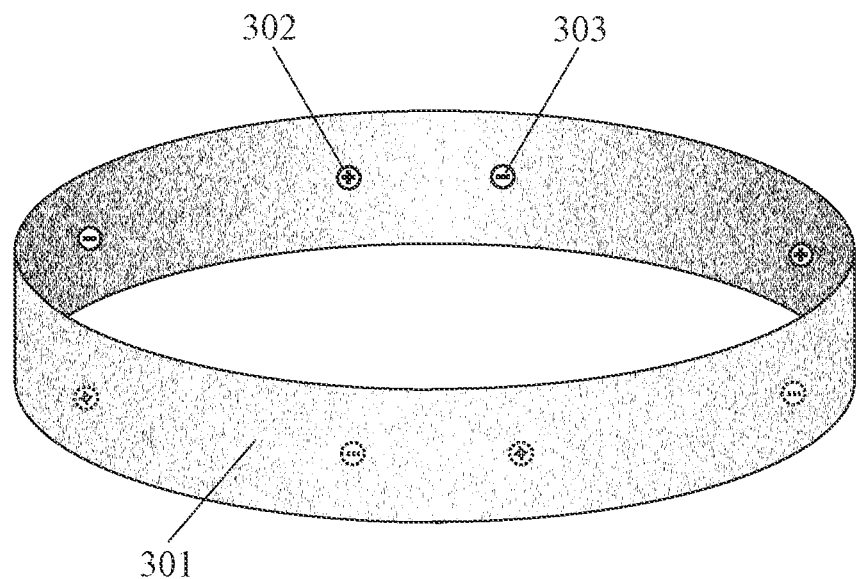
FIGS. 3 and 4 show two sequential views of a wearable ring wherein the circumferential location of a light emitter is automatically moved by the device.
Figure 4:
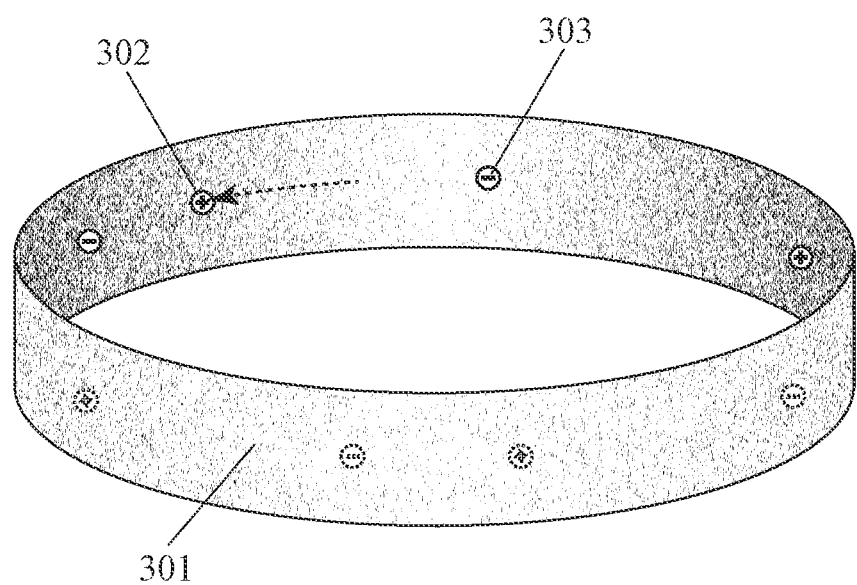

FIGS. 3 and 4 show two sequential views of an example of a wearable ring of biometric sensors comprising: a wearable ring 301 which is configured to be worn on a person's wrist, finger, or arm; an array of light emitters (including light emitter 302) and light receivers (including light receiver 303) which are configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In this example, the circumferential location of a light emitter on the circumference of the person's wrist, finger, or arm is automatically changed over time by the device. FIG. 3 shows light emitter 302 at a first circumferential location and FIG. 4 shows light emitter 302 having been automatically moved to a second circumferential location. In an example, a light emitter can be moved by an actuator along a (central) circumferential track or channel in the device. In an example, the circumferential location of a light emitter on the circumference of the person's wrist, finger, or arm can be automatically rotated around at least half of the circumference of the device. In an example, the circumferential location of a light emitter on the circumference of the person's wrist, finger, or arm can be automatically oscillated and/or iteratively-varied to scan different regions and/or depths of body tissue.

In an example, light emitters can be LEDs. In an example, light emitters can be lasers. In an example, different light emitters in the array can emit light energy with different wavelengths and/or spectra. In an example, different light emitters in the array can emit light energy at different angles or vectors with respect to the surface of the person's body. In an example, different light emitters in the array can emit light energy at different times.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

Figure 5:
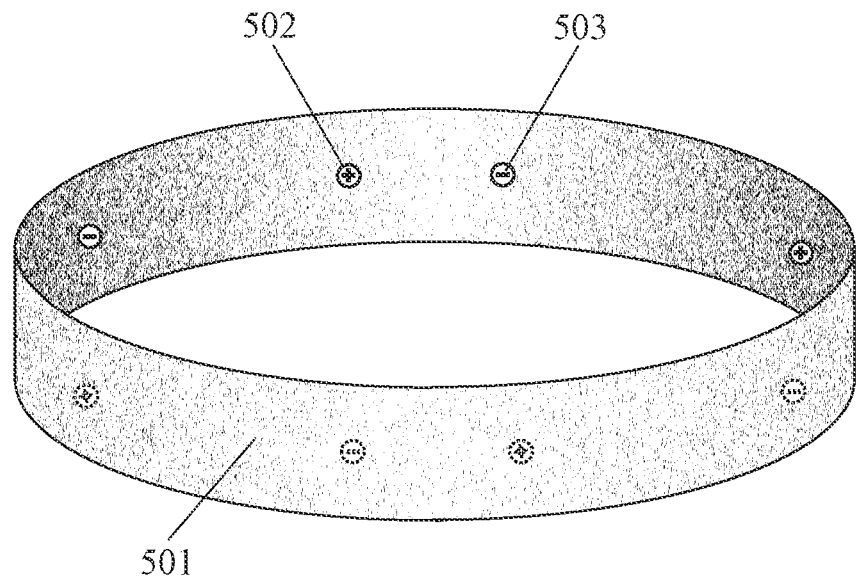
FIGS. 5 and 6 show two sequential views of a wearable ring wherein the circumferential location of a light receiver is automatically moved by the device.
Figure 6:
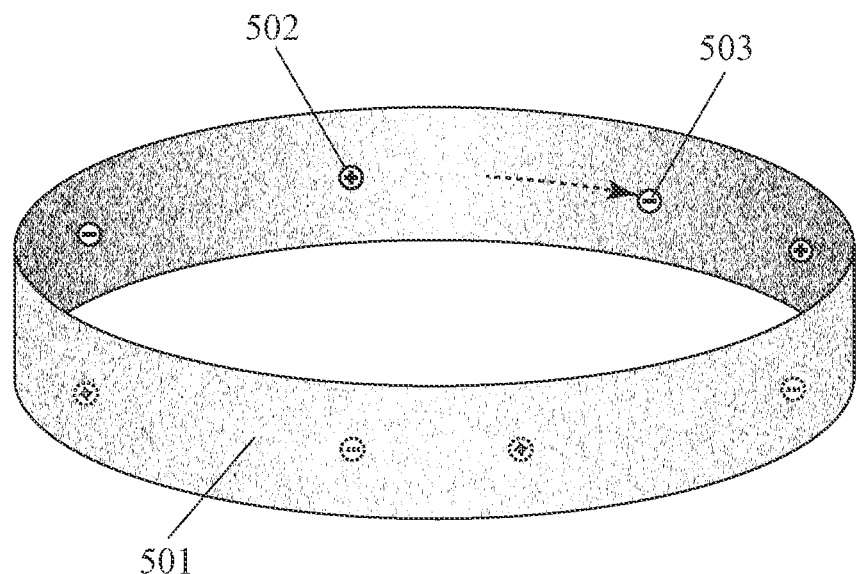

FIGS. 5 and 6 show two sequential views of an example of a wearable ring of biometric sensors comprising: a wearable ring 501 which is configured to be worn on a person's wrist, finger, or arm; an array of light emitters (including light emitter 502) and light receivers (including light receiver 503) which are configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In this example, the circumferential location of a light receiver on the circumference of the person's wrist, finger, or arm is automatically changed over time by the device. FIG. 5 shows light receiver 503 at a first circumferential location and FIG. 6 shows light receiver 503 having been automatically moved to a second circumferential location. In an example, a light receiver can be moved by an actuator along a (central) circumferential track or channel in the device. In an example, the circumferential location of a light receiver on the circumference of the person's wrist, finger, or arm can be automatically rotated around at least half of the circumference of the device. In an example, the circumferential location of a light receiver on the circumference of the person's wrist, finger, or arm can be automatically oscillated and/or iteratively-varied to scan different regions and/or depths of body tissue.

In an example, light emitters can be LEDs. In an example, light emitters can be lasers. In an example, different light emitters in the array can emit light energy with different wavelengths and/or spectra. In an example, different light emitters in the array can emit light energy at different angles or vectors with respect to the surface of the person's body. In an example, different light emitters in the array can emit light energy at different times.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

Figure 7:
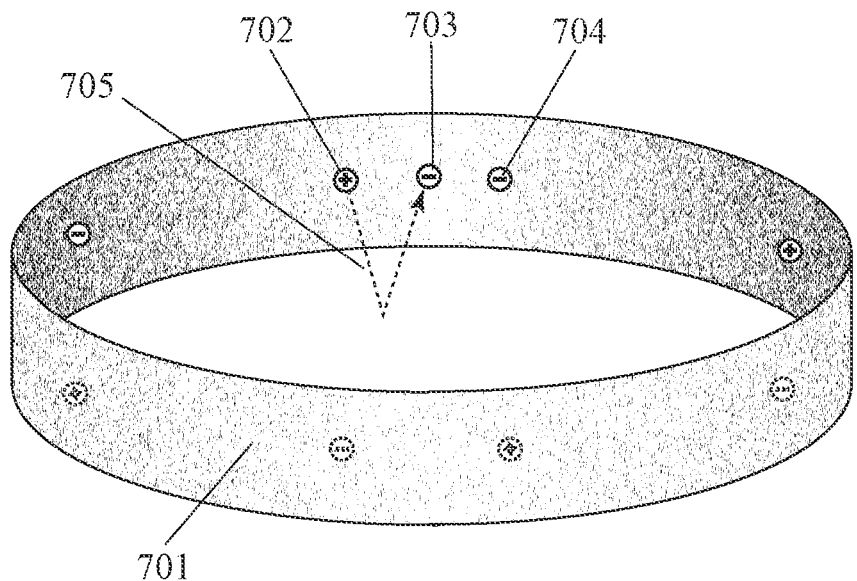
FIGS. 7 and 8 show two sequential views of a wearable ring wherein the angle of light which has been emitted from a light emitter is automatically changed by the device.
Figure 8:
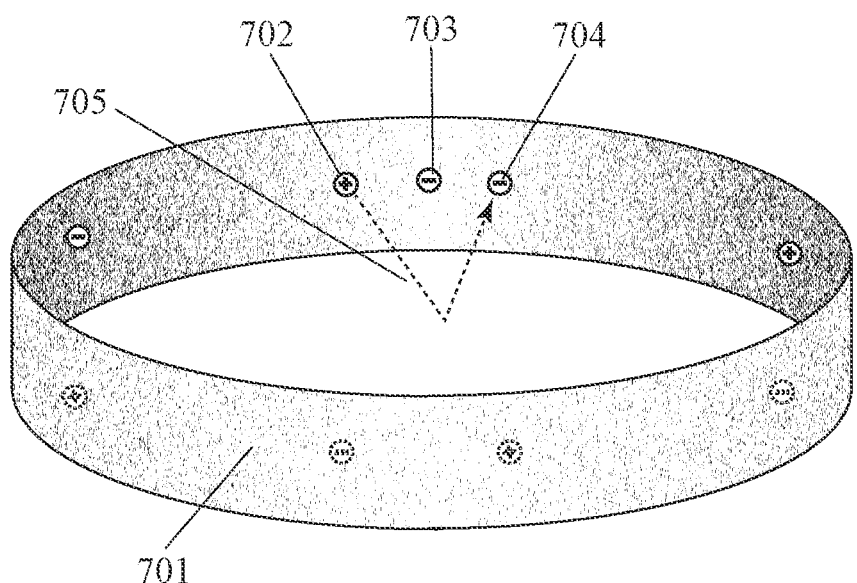

FIGS. 7 and 8 show two sequential views of an example of a wearable ring of biometric sensors comprising: a wearable ring 701 which is configured to be worn on a person's wrist, finger, or arm; an array of light emitters (including light emitter 702) and light receivers (including light receivers 703 and 704) which are configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In this example, the angle and/or vector of light emitted from light emitter 702 is automatically changed over time by the device. FIG. 7 shows the ring at a first time wherein light emitter 702 emits a beam of light 705 at a first angle and/or vector and wherein this beam of light is reflected by body tissue (not shown) toward light receiver 703. FIG. 8 shows the ring at a second time wherein light emitter 702 emits a beam of light 705 at a second angle and/or vector and wherein this beam of light is now reflected by body tissue (not shown) toward light receiver 704. In an example, a beam of light can be reflected from different regions and/or depths of body tissue by changing the angle and/or vector along which the beam of light is emitted. In an example, the angle and/or vector along which a light emitter emits beams of light can be automatically oscillated and/or iteratively-varied to scan different regions and/or depths of body tissue.

In an example, light emitters can be LEDs. In an example, light emitters can be lasers. In an example, different light emitters in the array can emit light energy with different wavelengths and/or spectra. In an example, different light emitters in the array can emit light energy at different angles or vectors with respect to the surface of the person's body. In an example, different light emitters in the array can emit light energy at different times.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

Figure 9:
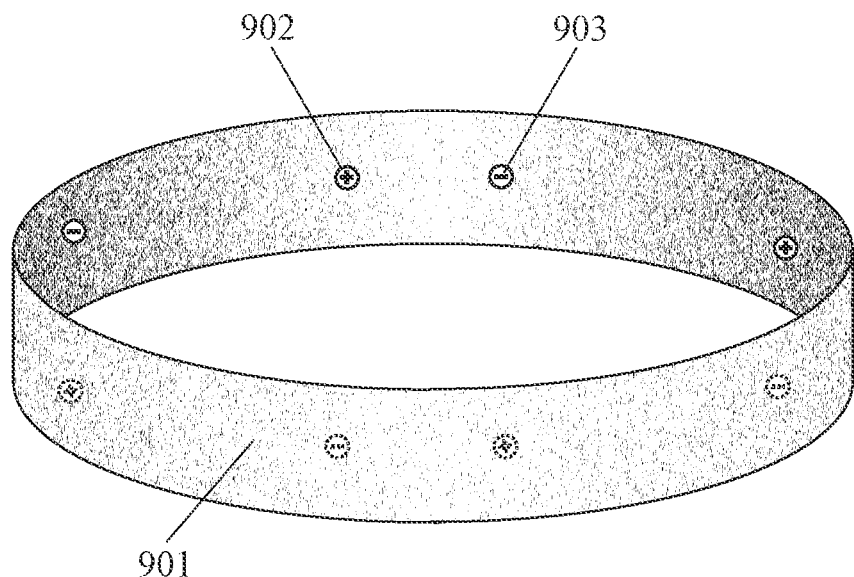
FIGS. 9 and 10 show two sequential views of a wearable ring wherein the distance between a light emitter and the surface of a person's body is automatically changed by the device.
Figure 10:
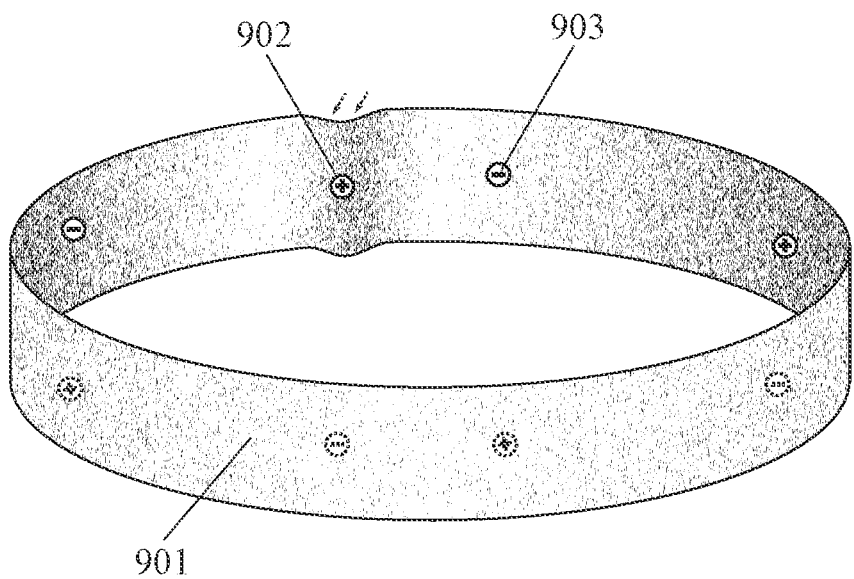

FIGS. 9 and 10 show two sequential views of an example of a wearable ring of biometric sensors comprising: a wearable ring 901 which is configured to be worn on a person's wrist, finger, or arm; an array of light emitters (including light emitter 902) and light receivers (including light receiver 903) which are configured to be worn around the person's wrist, finger, or arm; wherein the array of light emitters and light receivers is configured to collectively span at least half of the circumference of the person's wrist, finger, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In this example, the distance and/or pressure from a light emitter relative to a person's body (not shown) is automatically changed over time by the device. FIG. 9 shows the ring at a first time wherein light emitter 902 protrudes a first distance inward from the ring (e.g. into a first degree of contact and/or pressure with a person's body, not shown). FIG. 10 shows the ring at a second time wherein light emitter 902 protrudes a second distance inward from the ring (e.g. into a second degree of contact and/or pressure with the person's body, not shown). In an example, the distance and/or pressure from a light emitter relative to a person's body can be changed by inflation or deflation of a compartment on the ring. In an example, the distance and/or pressure from a light emitter relative to a person's body can be changed by an electromagnetic actuator on the ring. In an example, the distance and/or pressure from a light emitter relative to a person's can be automatically oscillated and/or iteratively-varied to scan different depths and/or regions of body tissue.

In an example, light emitters can be LEDs. In an example, light emitters can be lasers. In an example, different light emitters in the array can emit light energy with different wavelengths and/or spectra. In an example, different light emitters in the array can emit light energy at different angles or vectors with respect to the surface of the person's body. In an example, different light emitters in the array can emit light energy at different times.

In an example, this wearable ring can further comprise one or more additional components selected from the group consisting of: a data processor, a data transmitter/receiver, a power source, a display. In an example, this ring can further comprise (elastomeric and/or compressible) light shields between light emitters and light receivers. In an example, this wearable ring can be embodied in a wrist band. In an example, this wearable ring can be embodied in a fitness band. In an example, this wearable ring can be embodied in a smart watch. In an example, this wearable ring can be embodied in watch band. In an example, this wearable ring can be embodied in an arm band. In an example, this wearable ring can be embodied in the sleeve or cuff of a shirt. In an example, this wearable ring can be embodied in a finger ring. Relevant variations which are discussed in other portions of this disclosure or in priority-linked disclosures can also be applied to this example.

In an example, light emitters in the array can collectively span at least half of the circumference of the person's wrist, finger, or arm and light receivers in the array can also collectively span at least half of the circumference of the person's wrist, finger, or arm. In an example, light emitters in the array can collectively span at least three-quarters of the circumference of the person's wrist, finger, or arm and light receivers in the array can also collectively span at least three-quarters of the circumference of the person's wrist, finger, or arm.

In an example, a first light emitter in the array can be located in a first quadrant of the circumference of the person's wrist, finger, or arm; a second light emitter in the array can be located in a second quadrant of the circumference of the person's wrist, finger, or arm; and a third light emitter in the array can be located in a third quadrant of the circumference of the person's wrist, finger, or arm. In an example, the circumferential location of a light emitter on the circumference of the person's wrist, finger, or arm can be automatically changed over time by the device. In an example, the circumferential location of a light emitter on the circumference of the person's wrist, finger, or arm can be automatically rotated and/or moved around at least half of the circumference of the device. In an example, the circumferential location of a light emitter on the circumference of the person's wrist, finger, or arm can be automatically oscillated and/or iteratively-varied by the device.

In an example, a first light receiver in the array can be located in a first quadrant of the circumference of the person's wrist, finger, or arm; a second light receiver in the array can be located in a second quadrant of the circumference of the person's wrist, finger, or arm; and a third light receiver in the array can be located in a third quadrant of the circumference of the person's wrist, finger, or arm. In an example, the circumferential location of a light receiver on the circumference of the person's wrist, finger, or arm can be automatically changed over time by the device. In an example, the circumferential location of a light receiver on the circumference of the person's wrist, finger, or arm can be automatically rotated and/or moved around at least half of the circumference of the device. In an example, the circumferential location of a light receiver on the circumference of the person's wrist, finger, or arm can be automatically oscillated and/or iteratively-varied by the device.

In an example, a first light emitter in the array can emit light with first wavelength and/or spectrum and a second light emitter in the array can emit light with a second wavelength and/or spectrum. In an example, the wavelength and/or spectrum of light emitted by a light emitter can be automatically changed over time by the device. In an example, the wavelength and/or spectrum of light emitted by a light emitter can be automatically oscillated and/or iteratively-varied by the device.

In an example, a first light emitter in the array can emit light along first angle and/or vector with respect to the person's body and a second light emitter in the array can emit light along a second angle and/or vector with respect to the person's body. In an example, the angle and/or vector of light which has been emitted from a light emitter can be automatically changed over time by the device. In an example, the angle and/or vector of light which has been emitted from a light emitter can be automatically oscillated and/or iteratively-varied by the device.

In an example, a first light emitter in the array can be a first distance from the surface of a person's body and/or contact the person's body with a first pressure level and a second light emitter in the array can be a second distance from the surface of the person's body and/or contact the person's body with a second pressure level. In an example, the distance and/or pressure from a light emitter relative to the person's body can be automatically changed over time by the device. In an example, the distance and/or pressure from a light emitter relative to the person's body can be automatically oscillated and/or iteratively-varied by the device.

I claim:

1. A wearable ring of biometric sensors comprising:
a ring which is configured to be worn around a person's wrist, finger, or arm;
an array of light emitters and light receivers on the ring;
wherein the array of light emitters and light receivers further comprises a first light emitter, a second light emitter, a first light receiver, and a second light receiver; and
wherein light energy from one or more light emitters in the array which has passed through the person's body tissue and/or has been reflected from the person's body tissue and has been received by one or more light receivers in the array is analyzed in order to measure one or more biometric parameters selected from the group consisting of the person's oxygenation level, hydration level, glucose level, pulse rate, heart rate variability, and blood pressure; and
wherein the ring further comprises a plurality of electromagnetic actuators which are configured to automatically adjust distances and/or pressures, respectively, between the first light emitter and the person's wrist, finger, or arm; between the second light emitter and the person's wrist, finger, or arm; between the first light receiver and the person's wrist, finger, or arm; and between the second light receiver and the person's wrist, finger, or arm.

2. A wearable ring of biometric sensors comprising:
a ring which is configured to be worn around a person's wrist, finger, or arm;
an array of light emitters and light receivers on the ring;
wherein the array of light emitters and light receivers further comprises a first light emitter, a second light emitter, a first light receiver, and a second light receiver; and
wherein light energy from one or more light emitters in the array which has passed through the person's body tissue and/or has been reflected from the person's body tissue and has been received by one or more light receivers in the array is analyzed in order to measure one or more biometric parameters selected from the group consisting of the person's oxygenation level, hydration level, glucose level, pulse rate, heart rate variability, and blood pressure; and
wherein the ring further comprises: a first electromagnetic actuator which is configured to automatically adjust a distance and/or pressure between the first light emitter and the person's wrist, finger, or arm; a second electromagnetic actuator which is configured to automatically adjust a distance and/or pressure between the second light emitter and the person's wrist, finger, or arm; a third electromagnetic actuator which is configured to automatically adjust a distance and/or pressure between the first light receiver and the person's wrist, finger, or arm; and a fourth electromagnetic actuator which is configured to automatically adjust a distance and/or pressure between the second light receiver and the person's wrist, finger, or arm.

\* \* \* \* \*